(12) United States Patent
Kim et al.

(10) Patent No.: US 12,721,917 B2
(45) Date of Patent: Sep. 1, 2026

(54) CONTAINER STERILIZATION DEVICE USING PULSED LIGHT

(71) Applicant: IUCF-HYU (INDUSTRY-UNIVERSITY COOPERATION FOUNDATION HANYANG UNIVERSITY), Seoul (KR)

(72) Inventors: Young Beom Kim, Seoul (KR); Sung Keun Park, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 306 days.

(21) Appl. No.: 18/654,107

(22) Filed: May 3, 2024

(65) Prior Publication Data

US 2024/0374766 A1 Nov. 14, 2024

(30) Foreign Application Priority Data

May 10, 2023 (KR) ........................ 10-2023-0060360

(51) Int. Cl.

*A61L 2/084* (2026.01)
*A61L 2/24* (2006.01)
*A61L 103/00* (2026.01)

(52) U.S. Cl.

CPC ................. *A61L 2/084* (2013.01); *A61L 2/24* (2013.01); *A61L 2103/23* (2026.01);
(Continued)

(58) Field of Classification Search

CPC .......... A61L 2/082; A61L 2/084; A61L 2/085; A61L 2/10; A61L 2/101; A61L 2/102;
(Continued)

(56) References Cited

U.S. PATENT DOCUMENTS

2024/0197140 A1* 6/2024 Sperry ................ A47L 15/0089

FOREIGN PATENT DOCUMENTS

KR 20-2013-0006786 U 11/2013
KR 10-2016-0109836 A 9/2016
(Continued)

OTHER PUBLICATIONS

Communication dated Jun. 17, 2025, issued by the Korean Intellectual Property Office in Korean Application No. 10-2023-0060360.

*Primary Examiner* — Timothy C Cleveland
(74) *Attorney, Agent, or Firm* — Sughrue Mion, PLLC

(57) ABSTRACT

Disclosed is a device for sterilizing containers using pulsed light including a visible light band. The device includes: a housing provided with an openable door and providing an accommodation space therein; a container mounting area disposed on at least a portion of a bottom surface of the accommodation space; and a pulsed light generating lamp configured to be extended from the container mounting area toward an inside of the container, wherein a lower end of the pulsed light generating lamp is configured to be disposed lower than a lower end of the container mounted on the container mounting area.

14 Claims, 30 Drawing Sheets

(52) U.S. Cl.
CPC ...... *A61L 2202/11* (2013.01); *A61L 2202/121* (2013.01); *A61L 2202/122* (2013.01); *A61L 2202/17* (2013.01)

(58) Field of Classification Search
CPC . A61L 2/104; A61L 2/108; A61L 2/24; A61L 2103/20; A61L 2103/23; A61L 2202/11; A61L 2202/121; A61L 2202/122
See application file for complete search history.

(56) References Cited

FOREIGN PATENT DOCUMENTS

| | | | |
|---|---|---|---|
| KR | 10-2019-0018557 | A | 2/2019 |
| KR | 10-2019-0039176 | A | 4/2019 |
| KR | 20-0494512 | Y1 | 10/2021 |
| WO | 2017/004238 | A1 | 1/2017 |
| WO | 2018/020409 | A2 | 2/2018 |

* cited by examiner

FIG. 4

233 Capacitor charger
234
235 Trigger
200 Lamp (a)

233 Capacitor charger
234
236 Shimmer
200 Lamp (b)

10t
ds
200t
200
220
10s
230
920
210

2000

2010
2923
2913
2933
2943
2150
2200
2150
2921
2911
2931
2941

CONTAINER STERILIZATION DEVICE USING PULSED LIGHT

CROSS-REFERENCE TO RELATED APPLICATION

This application is based on and claims the benefit of priority to Korean Patent Application No. 10-2023-0060360, filed on May 10, 2023, the disclosure of which is incorporated herein in its entirety by reference.

BACKGROUND OF THE INVENTION

Field of the Invention

The present disclosure relates to a sterilization device, and more specifically, to a container sterilization device using pulsed light.

Related Art

The pandemic phenomenon has further heightened the public awareness of hygiene, and as a result, sterilization devices for various objects such as elevator buttons, escalator handles, and kiosk contact units are becoming widely available. In addition, as restrictions on the use of disposable containers inside food and beverage establishments have recently been implemented, personal hygiene measures for beverage containers are being required.

Conventionally, ultraviolet sterilization devices using UV-C have been generally used as devices for sterilizing objects, but such ultraviolet sterilization devices require irradiation of ultraviolet rays for a considerable period of time or longer for sterilization effect. Even in this case, there was controversy as to whether sufficient sterilization was performed.

SUMMARY OF THE INVENTION

One aspect of the present disclosure is directed to providing a sterilization device using pulsed light, such as intense pulsed light (IPL) or flash light, capable of achieving a high sterilization effect in a short time by instantly irradiating high energy pulsed light to an object to be sterilized.

Another aspect of the present disclosure is directed to providing a sterilization device capable of expecting a higher sterilization effect by minimizing the shaded area of pulsed light and controlling the distance from a lamp to an object to be sterilized to an appropriate distance in implementing a pulsed light-based sterilization device.

In addition, another aspect of the present disclosure is directed to providing a sterilization device capable of improving a sterilization effect by controlling the operation or configuration of the sterilization device adaptively to the material of an object to be sterilized.

In addition, another aspect of the present disclosure is directed to providing a stage or structure-integrated sterilization device that is integrated into a stage or structure and is able to easily perform sterilization and/or washing.

However, aspects of the present disclosure are not limited to the above, and various modifications are possible without departing from the spirit and scope of the present disclosure.

A container sterilization device using pulsed light according to one embodiment of the present disclosure is configured to sterilize a container using the pulsed light including a visible light band, and includes: a housing provided with an openable door and providing an accommodation space therein; a container mounting area disposed on at least a portion of a bottom surface of the accommodation space; and a pulsed light generating lamp configured to be extended from the container mounting area toward an inside of the container, wherein a lower end of the pulsed light generating lamp may be configured to be disposed lower than a lower end of the container mounted on the container mounting area.

According to one aspect, the pulsed light generating lamp may have a first electrode and a second electrode located at the lower end of the pulsed light generating lamp, and a light generating area between the first electrode and the second electrode protruded toward the inside of the container.

According to one aspect, the pulsed light generating lamp may have a ‘n’ shape.

According to one aspect, the pulsed light generating lamp may be a xenon lamp or a xenon lamp.

According to one aspect, the pulsed light generating lamp may be disposed so that upper ends of the first electrode and the second electrode are lower than the lower end of the container mounted on the container mounting area.

According to one aspect, the pulsed light generating lamp may be located inside the container mounting area and disposed in a recessed area formed to have a step with respect to a container contact area of the container mounting area.

According to one aspect, the container contact area of the container mounting area may be formed of a light-transmissive material.

According to one aspect, the pulsed light generating lamp may be configured to ascend or descend so that a distance between an upper end of the pulsed light generating lamp and a floor of an inner surface of the container reaches a first predetermined distance.

According to one aspect, at least a portion of the container contact area of the container mounting area may be configured to ascend or descend so that a distance between an upper end of the pulsed light generating lamp and a floor of an inner surface of the container reaches a first predetermined distance.

According to one aspect, there may be further included a mount holder that protrudes upward from the container mounting area to support the container while the container is spaced apart from the bottom surface of the accommodation space.

According to one aspect, the mount holder may be formed of a light-transmissive material.

According to one aspect, the pulsed light generating lamp may be configured to ascend or descend so that a distance between an upper end of the pulsed light generating lamp and a floor of an inner surface of the container reaches a first predetermined distance.

According to one aspect, the mount holder may be configured to ascend or descend so that a distance between an upper end of the pulsed light generating lamp and a floor of an inner surface of the container reaches a first predetermined distance.

A container sterilization device using pulsed light according to another embodiment of the present disclosure is configured to sterilize a container using the pulsed light including a visible light band, and includes: a housing provided with an openable door and providing an accommodation space therein; a container mounting area disposed on at least a portion of a bottom surface of the accommodation space; a pulsed light generating lamp configured to be extended from the container mounting area toward an inside of the container; and a container cover configured to surround the container on an outer surface of the container and block the pulsed light from the pulsed light generating lamp.

According to one aspect, the container sterilization device may be configured so that the container cover surrounds the container only in a sterilization mode for a light-transmissive container.

According to one aspect, the container cover may be provided separately from the housing.

According to one aspect, the container cover may be connected to at least one side surface of the accommodation space so that the location of the container cover may be changed.

According to one aspect, the container cover may be configured to: be connected to an inner ceiling of the accommodation space so that a disposition height of the container cover is adjustable; be descended to a first height in the sterilization mode for the light-transmissive container and surround the container on an outer surface of the container; and ascend and be located at a second height in the sterilization mode for a light-blocking container.

According to one aspect, the container cover may be configured to be deformable according to at least one of the shape or size of a container to be sterilized.

According to one aspect, the container cover may include: a first part having a floor unit and a side wall connected to the floor unit; and a second part having an additional side wall that is slidable upward and downward relative to the first part.

According to one aspect, the container cover may be configured so that an inner surface of the container cover contacts an outer surface of the container to be sterilized.

According to one aspect, the container cover may have a sponge unit on the inner surface of the container cover.

According to one aspect, the sponge unit may be configured of a metal sponge.

According to one aspect, the container cover may be provided with a plurality of flexible projections on the inner surface of the container cover.

According to one aspect, the pulsed light generating lamp may be operated so that an amount of energy transferred to the container to be sterilized is different depending on a material of the container.

According to one aspect, the pulsed light generating lamp may be operated so that the amount of energy transferred to the container to be sterilized is large in the order that the container is made of glass, plastic, ceramics, and metal.

According to one aspect, the pulsed light generating lamp may be configured to operate differently in at least one among the intensity of light pulse, the number of occurrences of the light pulse, and the generation interval of the light pulse depending on the material of the container to be sterilized.

A container sterilization device using pulsed light according to another embodiment of the present disclosure is configured to sterilize a container using the pulsed light including a visible light band, and includes: a housing formed of a light-blocking material and providing an accommodation space therein; a door formed of the light-blocking material and openably connected to the housing; a pulsed light generating lamp disposed within the accommodation space and configured to generate the pulsed light; and a slit configured to expose the pulsed light below a predetermined threshold value among the pulsed light emitted from the pulsed light generating lamp to the outside of the housing.

According to one aspect, the sterilization device may be configured to visualize the progress of a sterilization operation to a user of the sterilization device by exposing the pulsed light below the threshold value through the slit.

According to one aspect, the threshold value may be decided in consideration of an impact on the eyesight of a user of the sterilization device.

According to one aspect, the sterilization device may include at least one support unit configured to space the sterilization device from the ground, and the slit may include a downward slit that exposes the pulsed light toward the bottom surface of the sterilization device.

According to one aspect, the downward slit may be configured to expose the pulsed light toward the center of a ground area where the sterilization device is disposed.

According to one aspect, the slit may be configured to be closed under user control.

According to one aspect, the slit may be configured to control an amount of the pulsed light exposed to the outside of the housing under user control.

According to one aspect, the slit may be formed between the housing and the door based on a protrusion unit provided on at least one of the housing or the door.

According to one aspect, the protrusion unit may be configured so that the degree of protrusion may be changed according to user control.

According to one aspect, at least one of the housing or the door may be provided with a plurality of the protrusion units, and the plurality of protrusion units may be changed to different degrees of protrusion to control a pulsed light exposure direction of the slit formed between the housing and the door.

A container sterilization device using pulsed light according to another embodiment of the present disclosure is configured to sterilize a container using the pulsed light including a visible light band, and includes: a container mounting area disposed on a stage or structure; and a pulsed light generating lamp configured to be extended from the container mounting area toward the inside of the container, wherein the pulsed light generating lamp may be configured to generate the pulsed light in response to the container mounted on the container mounting area.

According to one aspect, there may be further included an illuminance sensor disposed in the container mounting area to be covered by the container, wherein the pulsed light generating lamp may be configured to generate the pulsed light in response to a decision that a illuminance sensing value measured by the illuminance sensor is below a predetermined threshold value.

According to one aspect, there may be further included a container cover configured to surround a light-transmissive container on an outer surface of the light-transmissive container and block the pulsed light from the pulsed light generating lamp in a sterilization mode for the light-transmissive container.

According to one aspect, there may be further included a lamp protection unit configured to surround the pulsed light generating lamp and protrude upward from the container mounting area to prevent the container from contacting the pulsed light generating lamp.

According to one aspect, the pulsed light generating lamp may be configured to: ascend and descend from the container mounting area; descend to be inserted into the container mounting area in response to a decision that the illuminance sensing value exceeds the predetermined threshold value; and ascend from the container mounting area toward the inside of the container in response to a decision that the illuminance sensing value is below the predetermined threshold value.

According to one aspect, there may be further included a receptacle located on the stage or structure and formed by being recessed to have a step with respect to an upper surface of the stage or structure, wherein the pulsed light generating lamp may be disposed inside the receptacle.

According to one aspect, the pulsed light generating lamp may be located inside the receptacle and disposed in a recessed area formed to have the step with respect to a container entrance contact area of the receptacle.

According to one aspect, there may be further included: at least one spray nozzle disposed inside the receptacle and spraying washing water toward the inside of the container; and an outlet for discharging liquid accumulated in the receptacle.

According to one aspect, the at least one spray nozzle may include a first spray nozzle that sprays the washing water in a first direction and a second spray nozzle that sprays the washing water in a second direction.

According to one aspect, there may be further included a blower disposed inside the receptacle and generating an air flow toward the inside of the container.

According to one aspect, in response to the container being mounted on the container mounting area, the container sterilization device may be configured to sterilize the container by the at least one spray nozzle spraying the washing water, the blower generating the air flow to remove the washing water inside the container, and the pulsed light generating lamp generating the pulsed light.

The disclosed technology can have the following benefits. However, it does not mean that a specific exemplary embodiment should include the entire following benefits or should include only the following benefits, and it should not be understood that the scope of the right of the disclosed technology is limited thereto.

According to the container sterilization device using pulsed light according to one embodiment of the present disclosure described above, a high sterilization effect can be achieved in a short time by instantaneously irradiating high energy pulsed light, such as the IPL or flash light, to an object to be sterilized.

In addition, in implementing a pulsed light-based sterilization device, a higher sterilization effect can be expected by minimizing the shaded area of pulsed light and controlling the distance from a lamp to an object to be sterilized to an appropriate distance.

Moreover, a sterilization effect can be improved by controlling the operation or configuration of the sterilization device adaptively to the material of an object to be sterilized.

According to a stage or structure-integrated sterilization device according to one embodiment of the present disclosure, the stage or structure-integrated sterilization device is integrated into a stage or structure and is able to easily sterilize and/or wash the container.

BRIEF DESCRIPTION OF THE DRAWINGS

FIG. 4 exemplarily shows a pulsed light generating circuit according to one embodiment.

DETAILED DESCRIPTION OF THE INVENTION

Figure 1:
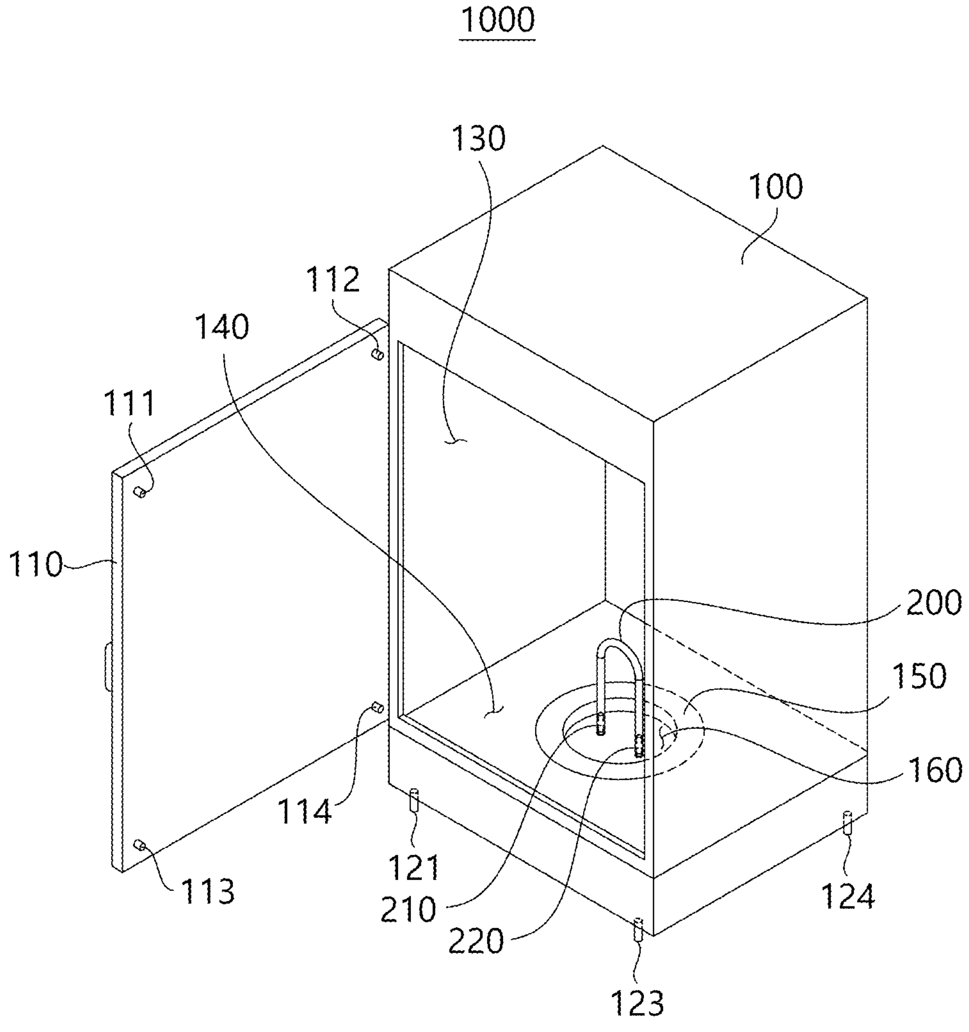
FIG. 1 is a schematic perspective view of a container sterilization device using pulsed light according to one embodiment of the present disclosure.

The present disclosure may be variously modified and have various types, and specific embodiments thereof will be illustrated in the drawings and described in detail in the detailed description.

However, this is not intended to limit the present disclosure to specific embodiments, and it should be understood that all modifications, equivalents, and substitutes included in the spirit and technical scope of the present disclosure are included.

Terms such as “first” and “second” may be used to describe various components, but the components are not restricted by the terms. The terms are used only to distinguish one component from another component. For example, a first component may be named a second component without departing from the scope of the right of the present disclosure. Likewise, a second component may be named a first component. The terms “and/or” may include combinations of a plurality of related described items or any of a plurality of related described items.

It will be understood that when a component is referred to as being “connected” or “coupled” to another component, the two components may be directly connected or coupled to each other, or intervening components may be present between the two components. It will be understood that when a component is referred to as being “directly connected or coupled”, no intervening components are present between the two components.

The terms used in the present specification are merely used to describe specific embodiments and are not intended to limit the present disclosure. A singular expression includes a plural expression, unless the context clearly states otherwise. In the present specification, it should be understood that the terms such as “include” or “have” are merely intended to indicate that features, numbers, steps, operations, components, parts, or combinations thereof are present, and are not intended to exclude the possibility that one or more other features, numbers, steps, operations, components, parts, or combinations thereof will be present or added.

Unless otherwise defined, all terms including technical and scientific terms used herein have the same meaning as commonly understood by those skilled in the technical field to which the present disclosure pertains. It will be understood that terms, such as those defined in commonly used dictionaries, should be interpreted as having meanings that are consistent with their meanings in the context of the relevant art and will not be interpreted in an idealized or overly formal sense unless expressly so defined herein.

Hereinafter, preferred embodiments of the present disclosure will be described in detail with reference to the accompanying drawings. In describing the present disclosure, in order to facilitate the overall understanding, the same reference numerals are used to designate the same components throughout the drawings, and repeated descriptions of the same components will be omitted.

Container Sterilization Device Using Pulsed Light

Figure 2:
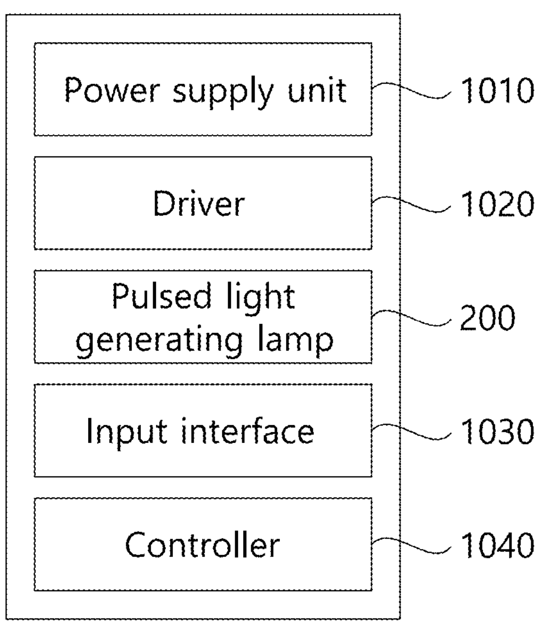
FIG. 2 is a block diagram illustrating the functional configuration of the container sterilization device using pulsed light of FIG. 1.

FIG. 1 is a schematic perspective view of a container sterilization device using pulsed light according to one embodiment of the present disclosure. FIG. 2 is a block diagram illustrating the functional configuration of the container sterilization device using pulsed light of FIG. 1. Hereinafter, a container sterilization device using pulsed light according to one embodiment of the present disclosure will be described in more detail with reference to FIGS. 1 and 2.

As illustrated in FIG. 1, a container sterilization device 1000 using pulsed light according to one embodiment of the present disclosure includes a housing 100, an openable door 110, and a pulsed light generating lamp 200.

The housing 100 is provided with the operable door 110 that, and an accommodation space 130 is provided inside the housing 100. A container mounting area 150 may be disposed on at least a portion of a bottom surface 140 of the accommodation space 130. In the drawings of the present disclosure, including FIG. 1, the container mounting area 150 is exemplarily illustrated as a circular shape, but the shape or size of the container mounting area 150 is not limited to the examples in the drawings. It should be understood that the container mounting area 150 may refer to any area disposed on the bottom surface of the accommodation space where a container is mounted. An installation area 160 for the pulsed light generating lamp may be located inside the container mounting area 150.

According to one aspect, at least one protrusion unit 111, 112, 113, or 114 is attached to the openable door 110, so that when the door 110 is closed, the protrusion unit 111, 112, 113, or 114 may be disposed between the housing 100 and the door 110.

A plurality of support units 121, 123, and 124 may be disposed on a bottom surface of the housing 100. Unlike the example shown in FIG. 1, the supports may be provided in various forms or numbers. Due to these supports, the bottom surface of the housing 100 may be located at a predetermined height or more from a floor surface where the sterilization device 1000 is disposed.

The pulsed light generating lamp 200 may be disposed to extend from the container mounting area 150 inside the housing 100 toward the inside of a container to be sterilized. In other words, the pulsed light generating lamp 200 of the sterilization device according to one embodiment of the present disclosure may be configured to be inserted toward the inside of the container to be sterilized. Accordingly, by being disposed closer to an inner surface of the container, a high sterilization effect on the inner surface of the container may be expected.

As illustrated in FIG. 2, the sterilization device 1000 according to one embodiment of the present disclosure may include a power supply unit 1010, a driver 1020, the pulsed light generating lamp 200, an input interface 1030, and a controller 1040.

For example, the power supply unit 1010 may refer to a power source that supplies energy necessary for the pulsed light generating lamp 200 to generate pulsed light.

As will be described in detail later in this description, the driver 1020 may represent, for example, a structure for causing the pulsed light generating lamp 200 or surrounding area to ascend or descend; a structure for changing the location of a container cover coupled to the device, or a configuration or structure for driving at least some configurations of the sterilization device 1000, such as at least one structure for adjusting the degree of protrusion of the protrusion unit of the door.

The pulsed light generating lamp 200 generates pulsed light to sterilize an object to be sterilized. The pulsed light generating lamp 200 may be, for example, a xenon lamp or a xenon lamp, but is not limited thereto, and it should be understood that any type of lamp for generating pulsed light is included in the technical spirit of the present disclosure.

The input interface 1030 includes a configuration for receiving input from a user to control at least one function of the sterilization device 1000 according to one embodiment of the present disclosure. For example, the input interface 1030 may include, but is not limited to, an input button or a touch screen.

The controller 1040 may include an arithmetic unit for controlling at least one configuration of the sterilization device 1000 according to one embodiment of the present disclosure. The controller 1040 may include, for example, a processor, and at least some of various arithmetic circuits may be included in the controller 1040.

For example, the configurations of the sterilization device 1000 as illustrate in FIG. 2 may be described in more detail along with a description of a plurality of embodiments in this description.

Intense Pulsed Light

The container sterilization device according to one embodiment of the present disclosure may be configured to sterilize containers using pulsed light including a visible light band. Herein, the pulsed light may include, for example, intense pulsed light (IPL) or flash light. Unlike conventional general sterilization devices that perform ultraviolet-based sterilization such as UV-C, the container sterilization device according to embodiments of the present disclosure may be configured to sterilize containers using pulsed light including the visible light band.

In order to expect a significant sterilization effect from a conventional sterilization device using UV-C, it was required to irradiate ultraviolet rays to an object to be sterilized for a considerable period of time. However, as in the sterilization device according to one embodiment of the present disclosure, the pulsed light with high energy is instantly emitted to sterilize the object to be sterilized, which has the favorable benefit of achieving a high sterilization effect while consuming a very short time.

Figure 3:
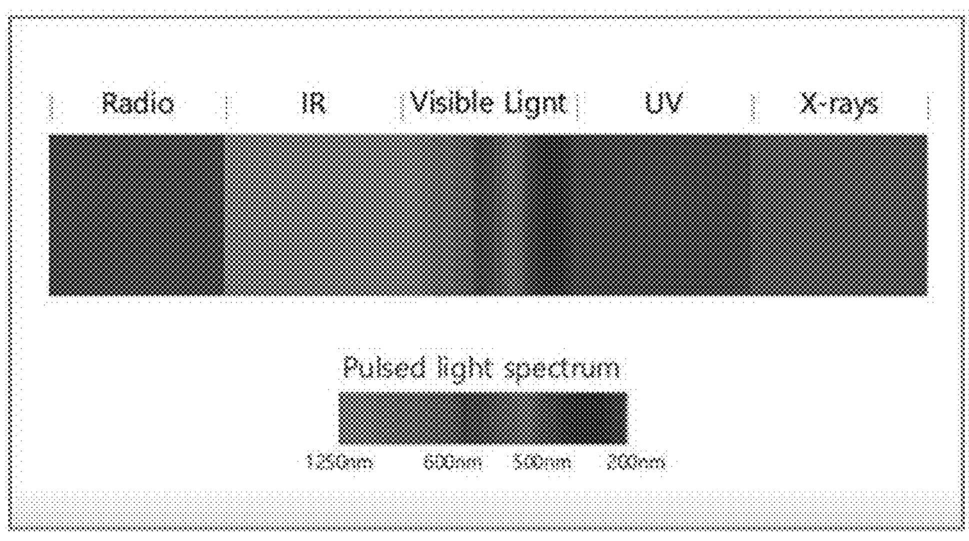
FIG. 3 shows an example spectrum of pulsed light.

In this regard, FIG. 3 shows an exemplary spectrum of pulsed light that may be applied according to one embodiment of the present disclosure. For example, unlike ultraviolet sterilization devices that use a UV-C wavelength band or laser equipment that only uses specific wavelength bands for specific purposes, the IPL may be a light pulse including light over a wide range of wavelengths, for example from 200 nm to 1250 nm. As described herein, the pulsed light may include an IPEL or a flash lamp, which is a powerful pulsed light, and may represent, for example, high-energy pulsed light that includes a wide wavelength band, including a visible light band.

Figure 4:
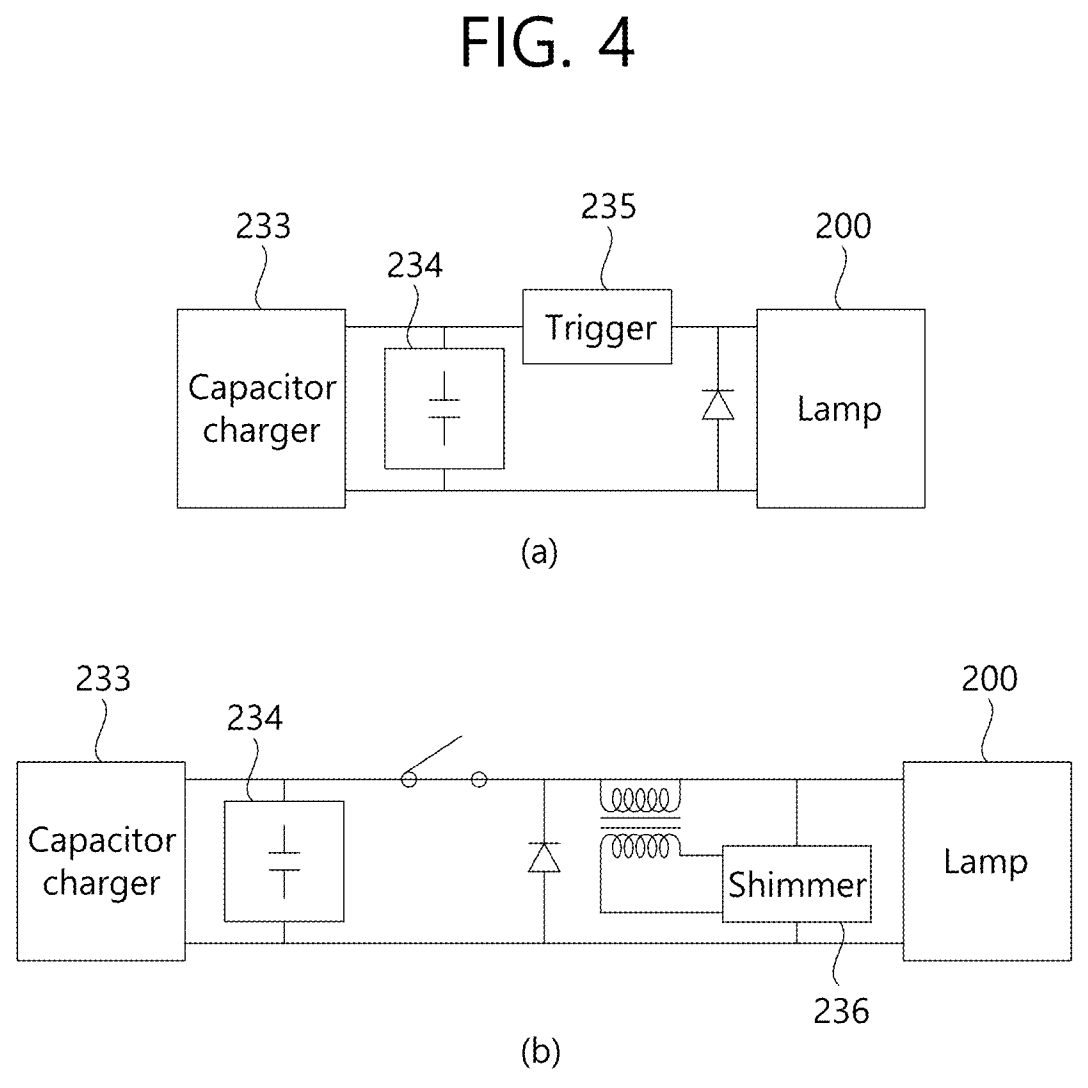

FIG. 4 exemplarily shows a pulsed light generating circuit according to one embodiment.

As illustrated in FIG. 4, the pulsed light generating lamp 200 that may be applied to the sterilization device according to one aspect of the present disclosure may be controlled by a strobe method that outputs pulsed light using a trigger voltage (or current) or a shimmer method that outputs pulsed light using a shimmer current (or voltage).

Referring to FIG. 4(A), the pulsed light generating lamp 200 may be controlled in a strobe manner. To this end, the pulsed light generating circuit may include a capacitor charger 233, a capacitor 234, and a trigger circuit unit 235. The strobe method emits light through the lamp 200 until all of the energy charged in the capacitor 234 is discharged, and has the advantage of excellent power efficiency and is not difficult to charge. However, the disadvantage is that the intensity of the output pulsed light is different for each, making detailed control difficult.

The capacitor charger 233 may charge the capacitor 234 according to a preset voltage. For example, the capacitor charger 233 may be a high-voltage capacitor charger. As the capacitor charger 233, a typical capacitor charger may be used, and detailed description is omitted.

The capacitor 234 may accumulate electrical energy charged by the capacitor charger 233.

The trigger circuit unit 235 may turn on the lamp 200 by discharging the charge charged in the capacitor 234 to the lamp 200 through a trigger voltage (or current). For example, the trigger circuit unit 235 may apply a high voltage (for example, about 10,000 to 20,000 volts) between an anode and cathode of the lamp 200 to ionize the gas in a pipe of the lamp 200 into a plasma state in order to turn on the lamp 200 from a non-lighting state. The gas ionized by the trigger circuit unit 235 may rapidly form a discharge path for high voltage and turn on the lamp 200. Bringing the lamp 200 from a non-lighting state to an initial lighting state is called a trigger, and the trigger circuit 235 may output pulsed light by repeating the blinking of the lamp 200 in a rapid cycle in this manner. The circuit of FIG. 4(A) including the trigger circuit unit 235 may be controlled, for example, by the controller 1040 of FIG. 2.

Referring to FIG. 4(B), the pulsed light generating lamp 200 may be controlled by a shimmer method, and the pulsed light generating circuit may include the capacitor charger 233, the capacitor 234, and a shimmer circuit unit 236. Hereinafter, descriptions that overlap with FIG. 4(A) will be omitted. In other words, technical ideas that may be dedicated to FIG. 4(A) are not repeatedly explained in FIG. 4(B).

The shimmer method is a method of controlling the emission amount of energy charged in the capacitor 234 to emit light through the lamp 200, and has the advantage of excellent lamp life and the ability to control the intensity of pulsed light, enabling detailed control. However, there is a disadvantage in that power efficiency is reduced because constant energy needs to always be maintained in the circuit through simmer current (or simmer voltage).

The shimmer circuit unit 236 may maintain the lamp 200 in a shimmer state. For example, the shimmer circuit unit 236 may flow a shimmer current, which is the minimum current required to keep the lamp 200 lit by the trigger voltage (or current) in a continuous lighting state. The lamp 200, which has presently been triggered and is in the shimmer state, may be turned on by being discharged when a voltage with large energy is applied from the capacitor 234 between the anode and the cathode. The circuit of FIG. 4(B) including the shimmer circuit unit 236 may be controlled, for example, by the controller 1040 of FIG. 2.

FIG. 4 is merely an example for convenience of explanation, and the circuit configuration for controlling the pulsed light generating lamp 200 according to the embodiments of the present disclosure is not limited thereto. According to some embodiments, configurations may be added to, excluded from, or subdivided from the environment of FIG. 4. For example, the control circuit may further include a transformer provided for insulation and voltage boosting, a diode for converting alternating current boosted through the transformer into direct current, and a switch.

Minimization of Shaded Areas

Figure 5:
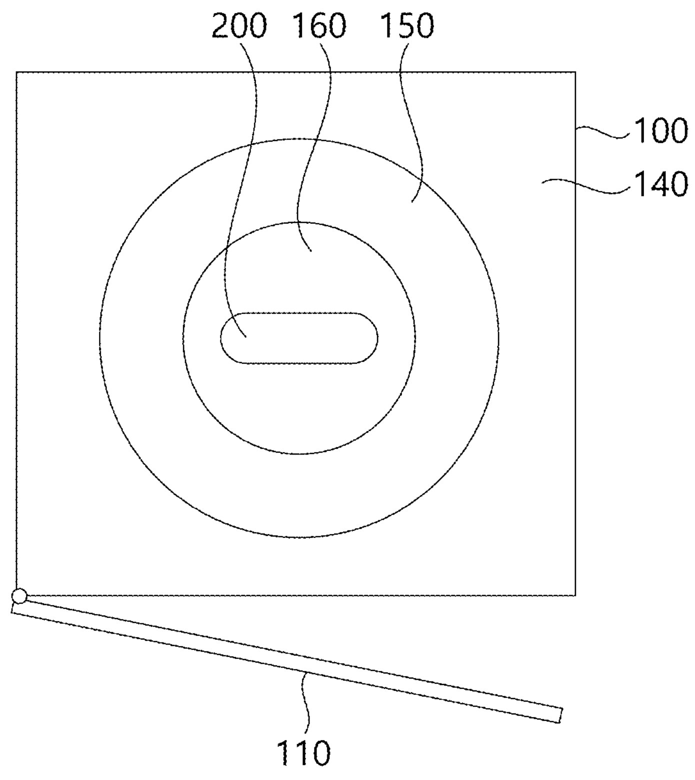
FIG. 5 is a top view of the container sterilization device using pulsed light according to one embodiment.

Referring again to FIG. 1, one embodiment of the sterilization device 1000 according to an one embodiment of the present disclosure will be described in more detail. In this regard, FIG. 5 is a top view of the container sterilization device using pulsed light according to one embodiment.

Figure 6:
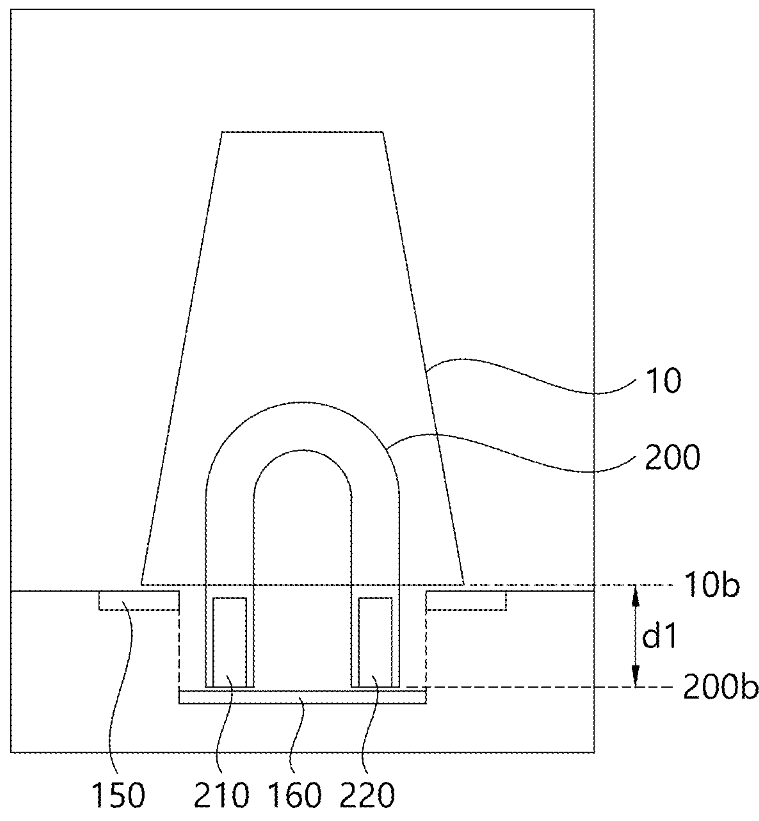
FIG. 6 is a side view of the container sterilization device using pulsed light according to one embodiment.

FIG. 6 is a side view of the container sterilization device using pulsed light according to one embodiment.

As illustrated in FIGS. 1 and 6, the pulsed light generating lamp 200 of the sterilization device 1000 according to one embodiment of the present disclosure includes a first electrode 210 and a second electrode 220. In general, for example, a pulsed light generating lamp such as a xenon lamp or xenon lamp is required to have electrodes of a certain size or larger in order to generate pulsed light based on high energy. In order to sterilize containers based on pulsed light as in one embodiment of the present disclosure, it may be desirable to arrange the distance between the light emitting area of the pulsed light generating lamp and a sterilizing target area within a predetermined interval to achieve an appropriate sterilization effect. In addition, since sterilization of the target area is performed based on pulsed light, minimizing the shaded area for pulsed light from the pulsed light generating lamp is required to improve the sterilization effect.

For example, when a general straight pulsed light generating lamp is applied to the sterilization device 1000 according to embodiments of the present disclosure and electrode units are disposed at both ends of the lamp, a shaded area of pulsed light is inevitably generated in an inner area of the container by means of a connection path between the electrode unit at one end and/or the corresponding electrode unit and the power supply unit.

Lamp Shape

According to one embodiment of the present disclosure, as illustrated in FIGS. 1 and 6, the first electrode 210 and the second electrode 220 of the pulsed light generating lamp 200 may be located at a lower end of the pulsed light generating lamp, and the light generating area between the first electrode and the second electrode may be configured to protrude toward the inside of the container. Accordingly, pulsed light may be irradiated over the entire inner surface of the container without a shaded area for irradiation of pulsed light inside the container.

As exemplarily illustrated in FIGS. 1 and 6, the pulsed light generating lamp 200 according to one aspect of the present disclosure may have a 'n' shape, but is not limited thereto. For example, the first electrode 210 and the second electrode 220 may be located at a lower end of the pulsed light generating lamp 200, and the light generating area between the electrodes may adopt the pulsed light generating lamp 200 having an arbitrary curved unit. As described above, the pulsed light generating lamp may be a xenon lamp or a xenon lamp, but is not limited to a specific type of pulsed light generating lamp. Any lamp capable of emitting pulsed light may be adopted.

Disposition of Electrode Units

Referring again to FIGS. 1 and 6, according to one embodiment of the present disclosure, the lower end of the pulsed light generating lamp 200 may be configured to be disposed lower than the lower end of the container mounted on the container mounting area 150. For example, the height of the installation area 160 of the pulsed light generating lamp may be configured to be lower than the height of the container mounting area 150.

As described above, in order to improve the sterilization effect by the pulsed light generating lamp 200, it may be required to minimize the shaded area of pulsed light irradiation and to maintain the distance between a pulsed light irradiation area and the container to be sterilized to a predetermined length or less. The pulsed light generating lamp may be provided with the electrode units 210 and 220 of a certain size and/or length or more in order to generate pulsed light using high energy. Even when the electrode units are disposed at the lower end of the pulsed light generating lamp, there may be restrictions on the distance from the container or the generation of a shaded area for pulsed light emission by the electrode units. According to one aspect of the present disclosure, a lower end 200*b* of the pulsed light generating lamp 200 may be configured to be disposed lower than a lower end 10*b* of the container mounted on the container mounting area 150. As illustrated in FIG. 6, according to one aspect, the lower end 200*b* of the pulsed light generating lamp 200 and the lower end 10*b* of the container may be disposed to have a height difference of more than a first distance d1. In other words, the height of the installation area 160 of the pulsed light generating lamp and the height of the container mounting area 150 may be disposed to have a difference of more than the first distance d1.

Figure 7:
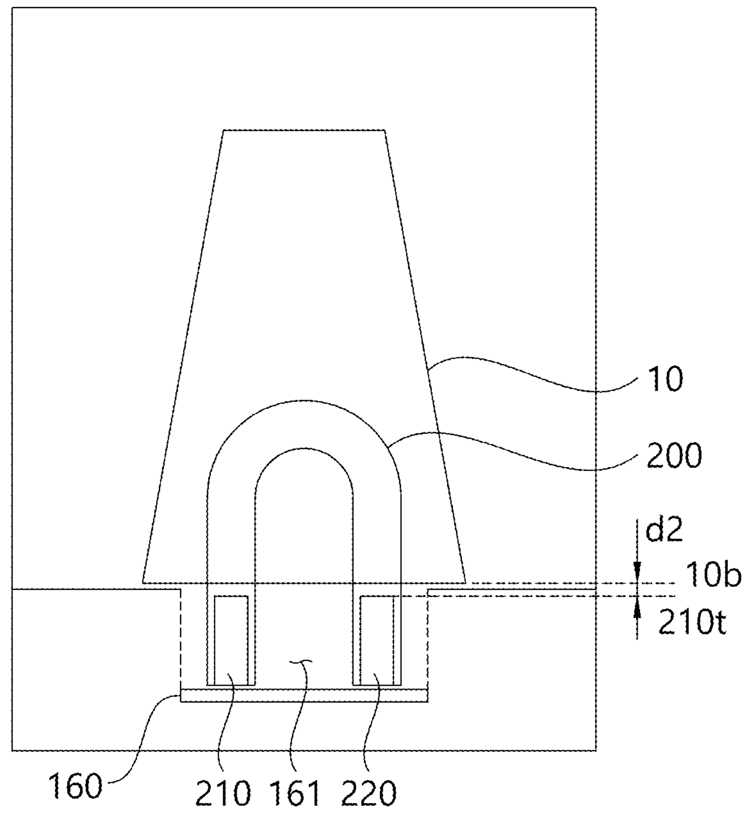
FIG. 7 is an illustration of a recessed area where a pulsed light generating lamp is disposed.

FIG. 7 is an illustration of a recessed area where a pulsed light generating lamp is disposed. More specifically, but non-limitingly, as illustrated in FIG. 7, the pulsed light generating lamp 200 may be located inside the container mounting area 150 and may be disposed in a recessed area 161 formed to have a step with respect to a container contact area of the container mounting area. For example, the installation area 160 of the pulsed light generating lamp may be a bottom surface of the recessed area 160.

According to one aspect, as illustrated in FIG. 7, the pulsed light generating lamp may be disposed so that upper ends 210*t* of the first electrode 210 and the second electrode 220 are lower than the lower end 10*b* of the container mounted on the container mounting area 150. For example, the pulsed light generating lamp 200 may be disposed so that the height difference between the lower end 10*b* of the container and the upper ends 210*t* of the first electrode 210 and the second electrode 220 is greater than or equal to a second distance d2. Accordingly, it is possible to ensure that no shaded area of pulsed light due to the electrode unit exists inside a container 10.

Figure 8:
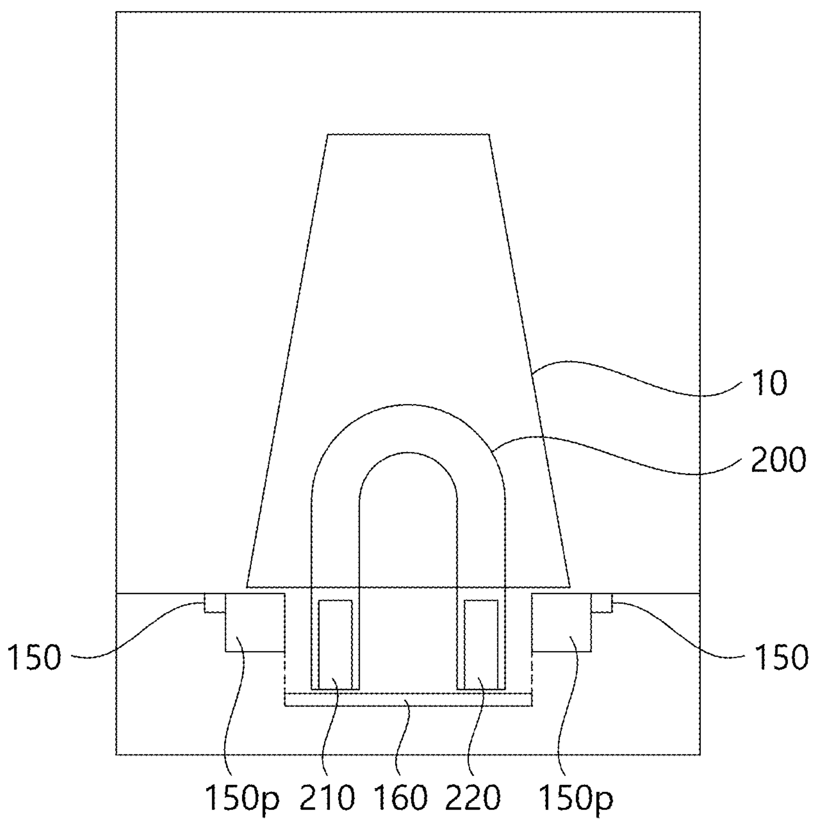
FIG. 8 is an illustration of a container contact area formed of a light-transmissive material.

FIG. 8 is an illustration of a container contact area formed of a light-transmissive material. As shown in FIG. 8, according to one aspect of the present disclosure, a container contact area 150*p* of the container mounting area 150 may be formed of a light-transmissive material. As such, when the container contact area 150*p* is formed of a light-transmissive material, the pulsed light emitted from the pulsed light generating lamp 200 may be irradiated even to the lowermost end of the container 10, thereby providing a sterilization effect even to the lowermost end of the container.

Container-Lamp Distance Control

As described above, the distance between the pulsed light generating lamp 200 and a sterilization target area may also be considered important for improving the sterilization effect. According to one aspect of the present disclosure, at least one of the configurations for controlling the distance between the container and the lamp may be adopted in consideration of the size and/or shape of the container to be sterilized.

Figure 9:
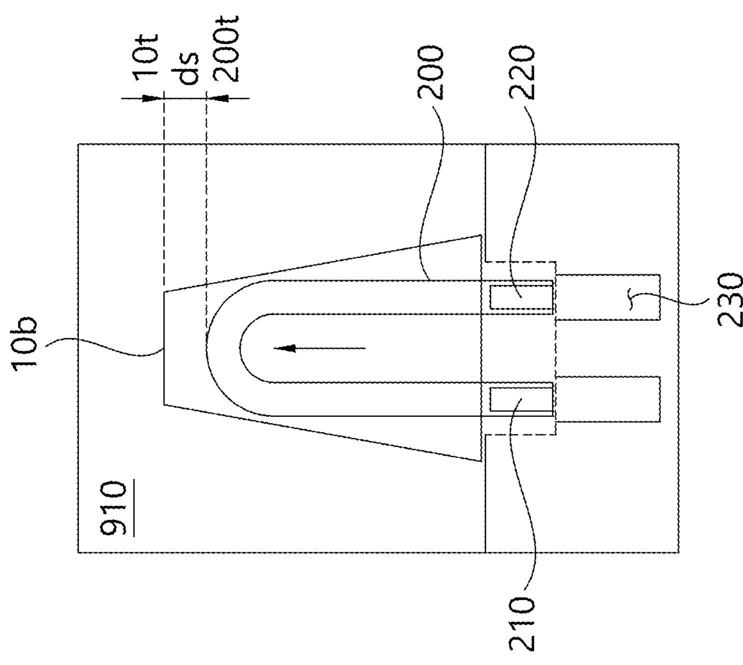
FIG. 9 illustrates an exemplary configuration in which a pulsed light generating lamp ascends or descends to control the distance between a container and a lamp.

FIG. 9 illustrates an exemplary configuration in which a pulsed light generating lamp ascends or descends to control the distance between a container and a lamp. For example, the pulsed light generating lamp may be configured to ascend or descend so that the distance between an upper end of the pulsed light generating lamp and a floor of an inner surface of the container reaches a first predetermined distance.

In other words, as illustratively shown in FIG. 9, according to one embodiment of the present disclosure, with the container 10 mounted on the container mounting area 150, the pulsed light generating lamp 200 ascends or descends depending on the size and/or shape of the container 10, allowing the distance between a height 10*t* of a bottom surface of the container 10 and a height 200*t* of the upper end of the pulsed light generating lamp 200 to be adjusted to a predetermined appropriate distance ds. According to one aspect, a lamp accommodation unit 230 in which the lamp may descend and be stored may be provided at a lower portion of the lamp installation area.

More specifically, as illustrated in FIG. 9, for example, when a relatively large-sized container 10*b* is mounted on the container mounting area (910), the pulsed light generating lamp 200 may ascend from the lamp accommodation unit 230 so that the distance between the height 200*t* of an upper end of the lamp and the height 10*t* of the bottom surface of the container is set to the appropriate distance ds.

In addition, for example, when a relatively small-sized container 10*s* is mounted on the container mounting area (920), the pulsed light generating lamp 200 may descend toward the lamp accommodation unit 230 so that the distance between the height 200*t* of the upper end of the lamp and the height 10*t* of the bottom surface of the container is set to the appropriate distance ds.

The ascending or descending of the pulsed light generating lamp 200 may be performed by the driver 1020 as illustrated in FIG. 2. According to one aspect, for example, a sensor for measuring the distance between the upper end of the pulsed light generating lamp 200 and the bottom surface of the container, such as a laser sensor, may be provided. By being provided with electric ascending and descending members such as rack gear/pinion gear and motor, the ascending or descending of the pulsed light generating lamp 200 may be automatically performed adaptively according to the size and/or shape of the container. However, the configuration of the driver 1020 is not limited thereto, and a structure for manually controlling the height of the pulsed light generating lamp 200 by a user of the sterilization device 1000 may be adopted.

Figure 10:
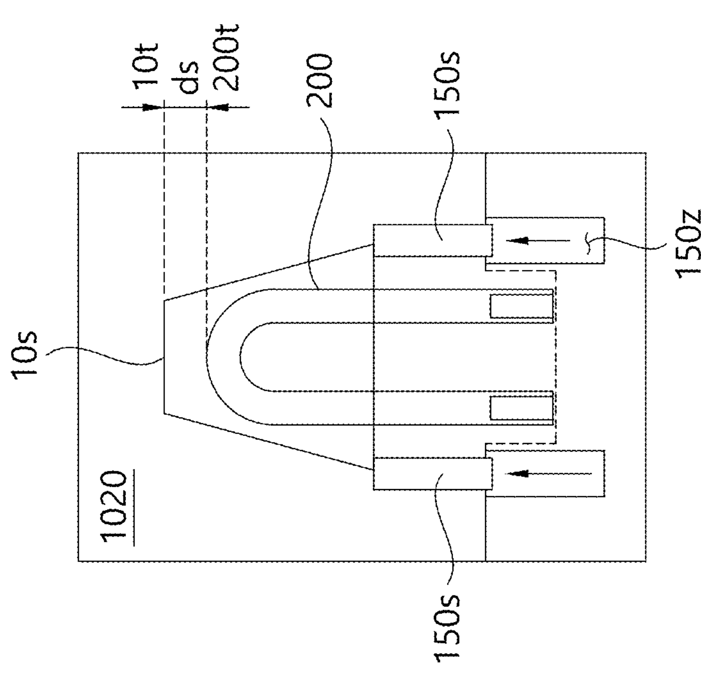
FIG. 10 illustrates an exemplary configuration in which at least a portion of the container contact area ascends or descends to control the distance between the container and the lamp.

FIG. 10 illustrates an exemplary configuration in which at least a portion of the container contact area ascends or descends to control the distance between the container and the lamp. For example, at least a portion of the container contact area of the container mounting area may be configured to ascend or descend so that the distance between the upper end of the pulsed light generating lamp and the floor of the inner surface of the container reaches a first predetermined distance.

In other words, as illustratively illustrated in FIG. 10, according to one embodiment of the present disclosure, with the container 10 mounted on the container mounting area 150, the at least a portion 150*s* of the container contact area ascends or descends depending on the size and/or shape of the container 10, allowing the distance between a height 10*t* of the bottom surface of the container 10 and a height 200*t* of the upper end of the pulsed light generating lamp 200 to be adjusted to the predetermined appropriate distance ds. According to one aspect, an ascending and descending structure accommodation unit 150*z* in which the at least a portion 150*s* of the container contact area may descend and be stored may be provided at a lower portion of the container contact area.

More specifically, as illustrated in FIG. 10, for example, when the relatively large-sized container 10*b* is mounted on the container mounting area (1010), the at least a portion 150*s* of the container contact area may ascend from the ascending and descending structure accommodation unit 150*z* so that the distance between the height 200*t* of the upper end of the lamp and the height 10*t* of the bottom surface of the container is set to the appropriate distance ds.

In addition, for example, when the relatively small-sized container 10*s* is mounted on the container mounting area (1020), the at least a portion 150*s* of the container contact area may descend toward the ascending and descending structure accommodation unit 150*z* so that the distance between the height 200*t* of the upper end of the lamp and the height 10*t* of the bottom surface of the container is set to the appropriate distance ds.

The ascending or descending of the at least a portion 150*s* of the container contact area may be performed by the driver 1020 as illustrated in FIG. 2. According to one aspect, for example, a sensor for measuring the distance between the upper end of the pulsed light generating lamp 200 and the bottom surface of the container, such as a laser sensor, may be provided. By being provided with electric ascending and descending members such as rack gear/pinion gear and motor, the ascending or descending of the at least a portion 150*s* of the container contact area may be automatically performed adaptively according to the size and/or shape of the container. However, the configuration of the driver 1020 is not limited thereto, and a structure for manually controlling the height of the at least a portion 150*s* of the container contact area by a user of the sterilization device 1000 may be adopted.

Figure 11:
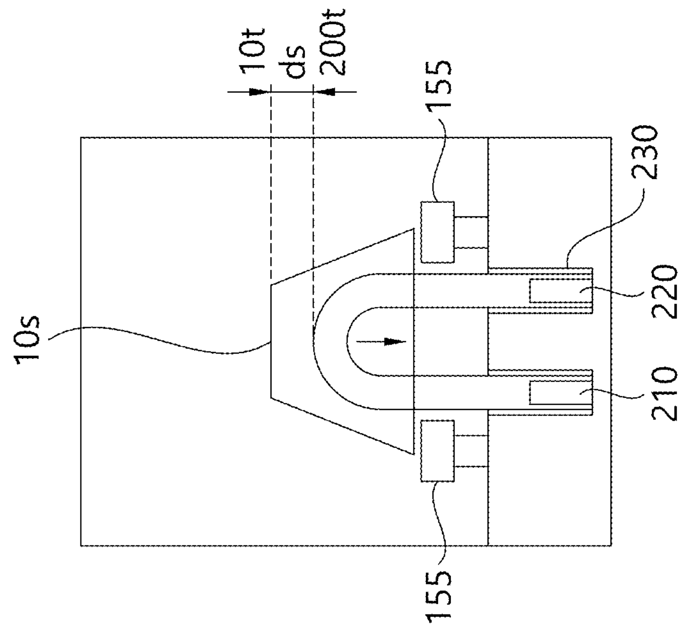
FIG. 11 illustrates an exemplary configuration in which a pulsed light generating lamp ascends or descends to control the disposition of a container mount holder and the distance between the container and the lamp according to one aspect.
Figure 11:
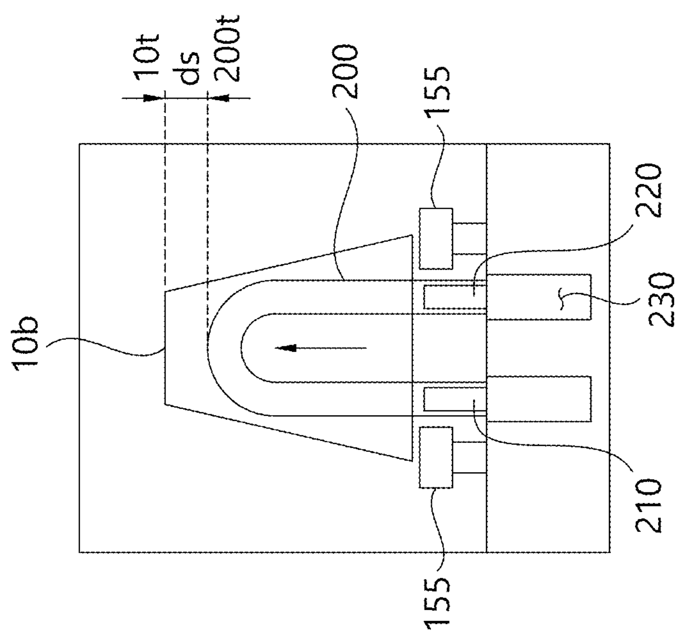

FIG. 11 illustrates an exemplary configuration in which a pulsed light generating lamp ascends or descends to control the disposition of a container mount holder and the distance between the container and the lamp according to one aspect.

First, as illustrated in FIG. 11, according to one embodiment of the present disclosure, the sterilization device 1000 may further include a mount holder 155 that protrudes upward from the container mounting area 150 and supports the container 10 while being spaced apart from the bottom surface of the accommodation space inside the housing 100. Accordingly, it is possible to ensure that the shaded area of the pulsed light generated by the electrode units 210 and 220 of the pulsed light generating lamp 200 is not located inside the container 10 to be sterilized. According to one aspect, the height of the mount holder 155 may be determined so that the uppermost end of the mount holder 155 is located higher than the uppermost end of the electrode units 210 and 220.

For example, the mount holder may be formed of a light-transmissive material. Accordingly, it is possible to prevent the generation of a shaded area for pulsed light from the pulsed light generating lamp 200 that may be generated by the mount holder. In addition, according to one aspect, the mount holder 155 is manufactured in the shape of a comb tooth with an empty space inside, such as a handle shape, to minimize the contact area between the container 10 and the mount holder 155 and to maximize the area where pulsed light from the pulsed light generating lamp 200 is directly irradiated to the container 10.

Referring again to FIG. 11, even when the mount holder 155 is provided, in a similar sense as previously described with reference to FIG. 9, for example, the pulsed light generating lamp may be configured to ascend or descend so that the distance between the upper end of the pulsed light generating lamp and the floor of the inner surface of the container reaches a first predetermined distance.

In other words, as exemplarily illustrated in FIG. 11, according to one embodiment of the present disclosure, with the container 10 mounted on the mount holder 155, the pulsed light generating lamp 200 ascends or descends depending on the size and/or shape of the container 10, thereby adjusting the distance between the height 10*t* of the bottom surface of the container 10 and the height 200*t* of the upper end of the pulsed light generating lamp 200 to the predetermined appropriate distance ds. According to one aspect, the lamp accommodation unit 230 in which the lamp may descend and be stored may be provided at the lower portion of the lamp installation area.

More specifically, as illustrated in FIG. 11, for example, when the relatively large-sized container 10*b* is mounted on the mount holder, the pulsed light generating lamp 200 may ascend from the lamp accommodation unit 230 so that the distance between the height 200*t* of the upper end of the lamp and the height 10*t* of the bottom surface of the container is set to the appropriate distance ds.

In addition, for example, when the relatively small-sized container 10*s* is mounted on the mount holder, the pulsed light generating lamp 200 may descend toward the lamp accommodation unit 230 so that the distance between the height 200*t* of the upper end of the lamp and the height 10*t* of the bottom surface of the container is set to the appropriate distance ds.

The ascending or descending of the pulsed light generating lamp 200 may be performed by the driver 1020 as illustrated in FIG. 2. According to one aspect, for example, a sensor for measuring the distance between the upper end of the pulsed light generating lamp 200 and the bottom surface of the container, such as a laser sensor, may be provided. By being provided with electric ascending and descending members such as rack gear/pinion gear and motor, the ascending or descending of the pulsed light generating lamp 200 may be automatically performed adaptively according to the size and/or shape of the container. However, the configuration of the driver 1020 is not limited thereto, and a structure for manually controlling the height of the pulsed light generating lamp 200 by a user of the sterilization device 1000 may be adopted.

Figure 12:
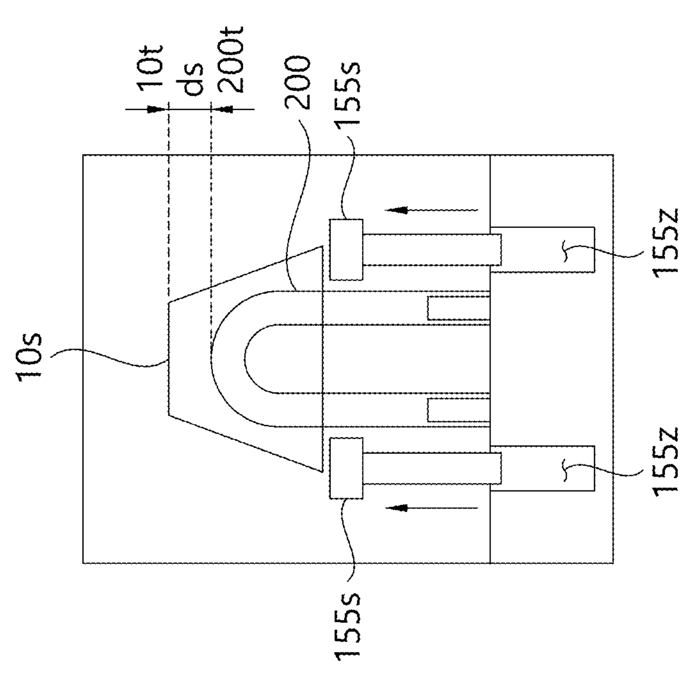
FIG. 12 illustrates an exemplary configuration in which the container mount holder ascends or descends to control the distance between the container and the lamp.
Figure 12:
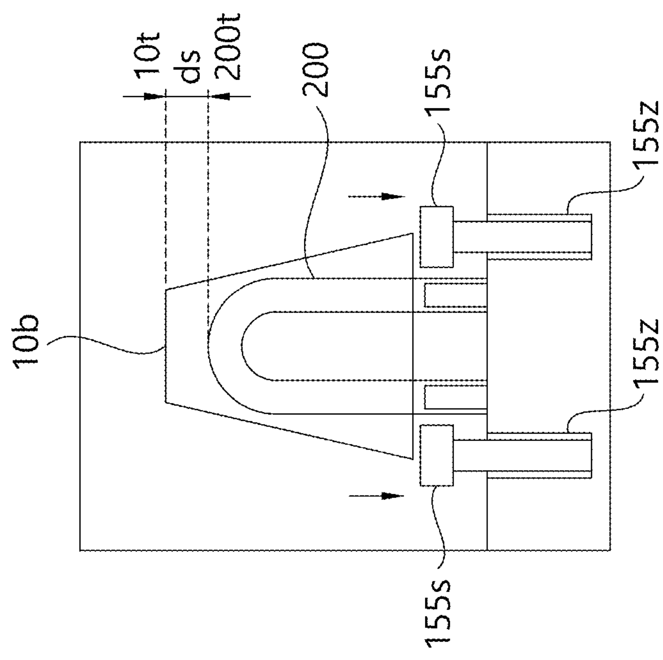

FIG. 12 illustrates an exemplary configuration in which the container mount holder ascends or descends to control the distance between the container and the lamp. For example, the mount holder may be configured to ascend or descend so that the distance between the upper end of the pulsed light generating lamp and the floor of the inner surface of the container reaches a first predetermined distance.

In other words, as exemplarily illustrated in FIG. 12, according to one embodiment of the present disclosure, with the container 10 mounted on a container mount holder 155*s*, the container mount holder 155*s* ascends or descends depending on the size and/or shape of the container 10, thereby adjusting the distance between the height 10*t* of the bottom surface of the container 10 and the height 200*t* of the upper end of the pulsed light generating lamp 200 to the predetermined appropriate distance ds. According to one aspect, a mount holder accommodation unit 155*z* in which the container mount holder 155*s* descend and be stored may be provided at the lower portion of the container mount holder 155*s*.

More specifically, as illustrated in FIG. 12, for example, when the relatively large-sized container 10*b* is mounted on the container mount holder, the container mount holder 155*s* may ascend from the mount holder accommodation unit 155*z* so that the distance between the height 200*t* of the upper end of the lamp and the height 10*t* of the bottom surface of the container is set to the appropriate distance ds.

In addition, for example, when the relatively small-sized container 10*s* is mounted on the container mount holder, the container mount holder 155*s* may descend toward the mount holder accommodation unit 155*z* so that the distance between the height 200*t* of the upper end of the lamp and the height 10*t* of the bottom surface of the container is set to the appropriate distance ds.

The ascending or descending of the container mount holder 155*s* may be performed by the driver 1020 as illustrated in FIG. 2. According to one aspect, for example, a sensor for measuring the distance between the upper end of the pulsed light generating lamp 200 and the bottom surface of the container, such as a laser sensor, may be provided. By being provided with electric ascending and descending members such as rack gear/pinion gear and motor, the ascending or descending of the container mount holder 155*s* may be automatically performed adaptively according to the size and/or shape of the container. However, the configuration of the driver 1020 is not limited thereto, and a structure for manually controlling the height of the container mount holder 155*s* by a user of the sterilization device 1000 may be adopted.

Cover for Light-Transmissive Container

As described above, the sterilization device according to one embodiment of the present disclosure may be configured to sterilize containers using pulsed light including a visible light band. Unlike conventional ultraviolet-based sterilization, pulsed light-based sterilization using instantaneous high-energy emission, for example, the IPL, performs sterilization on an object in a very short period of time. In this connection, the researchers of the present disclosure have discovered that the sterilization effect may differ depending on the material of the object to be sterilized, and in particular, when pulsed light is irradiated to a light-transmitting material, the sterilization effect may be reduced compared to the case of a material that does not transmit light.

Figure 13:
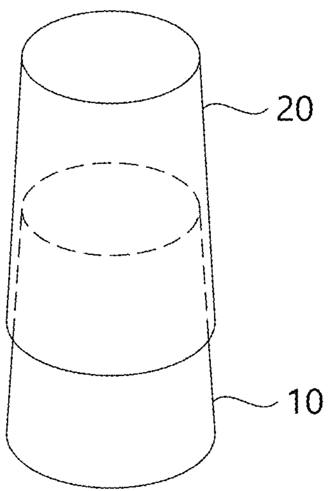
FIG. 13 is a conceptual view of a container cover according to one embodiment of the present disclosure.

To address this issue, the sterilization device according to one embodiment of the present disclosure may be provided with a container cover that surrounds the container to be sterilized and blocks pulsed light. FIG. 13 is a conceptual view of a container cover according to one embodiment of the present disclosure. As illustrated in FIG. 13, a container cover 20 may be provided to surround an outer surface of the container 10 to be sterilized and block pulsed light emitted from the pulsed light generating lamp extending into an inside of the container 10.

As illustrated again in FIG. 1, the sterilization device 1000 according to one embodiment of the present disclosure is configured to sterilize a container using the pulsed light including a visible light band, and includes: the housing 100 provided with an openable door and providing the accommodation space therein; the container mounting area 150 disposed on at least a portion of a bottom surface of the accommodation space; and the pulsed light generating lamp 200 configured to be extended from the container mounting area toward the inside of the container. Furthermore, as illustrated in FIG. 13, the container cover 20 may be further provided on the outer surface of the container to surround the container 10 and block pulsed light from the pulsed light generating lamp 200.

According to one aspect of the present disclosure, the container sterilization device may be configured so that the container cover 20 surrounds the container 10 only in a sterilization mode for a light-transmissive container. In other words, the container sterilization device may be provided with different sterilization modes depending on the material of the container, for example, and may apply the container cover only when the light-transmissive container is sterilized so that pulsed light generated inside the container is blocked through the container cover. Accordingly, it is possible to prevent a decrease in the effectiveness of pulsed light-based sterilization for light-transmissive materials.

The container cover may be provided in various forms. For example, as illustrated in FIG. 13, the container cover 20 may be provided separately from the housing 100. In other words, the container cover 20 may be provided as one of the package configurations of the sterilization device, but may be provided separately from the housing, so that a user may directly cover the container and use the same only when necessary for sterilizing the light-transmissive container. The sterilization device according to one embodiment of the present disclosure may be customized according to the purpose or characteristics of the place of use. As one of the user-specific configurations, for example, when the sterilization device is to be used in a specific food and beverage manufacturing facility, the container cover with a shape optimized to be applied to the container used at the corresponding facility may be provided.

Figure 14:
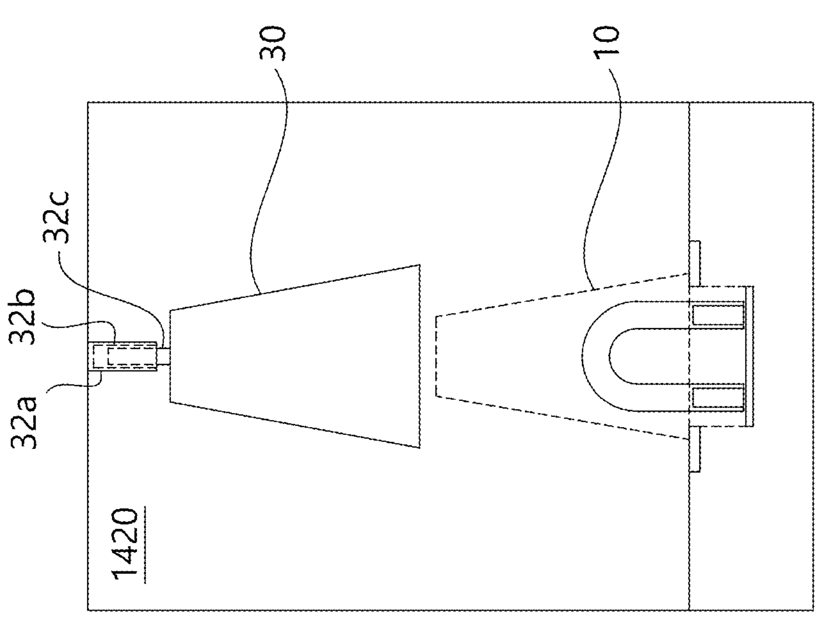
FIG. 14 is an exemplary view of a location variable container cover coupled to a device according to one embodiment.
Figure 14:
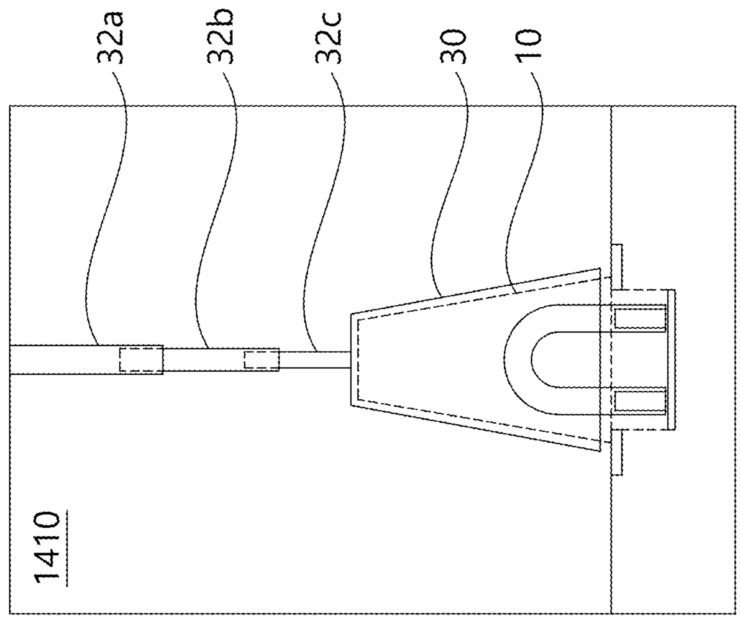

FIG. 14 is an exemplary view of a location variable container cover coupled to a device according to one embodiment. According to one aspect of the present disclosure, as illustrated in FIG. 14, a container cover 30 may be connected to at least one side surface of the accommodation space of the housing 100 so that the location of the container cover may be changed. In other words, the container cover 30 is provided coupled to a predetermined location of the sterilization device, but the location of the container cover may be freely adjusted so as to be applied or not to be applied to the container as needed.

For example, as illustrated in FIG. 14, the container cover 30 may be connected to an inner ceiling of the accommodation space inside the housing 10 so that the disposition height of the container cover 30 may be adjusted. For example, the container cover 30 may be fixed to the ceiling inside the housing 10 by a support having a plurality of support parts, such as a first support part 32*a*, a second support part 32*b* configured to be adjustable in relative height in relation to the first support part, and a third support part 32*c* configured to be adjustable in relative height in relation to the second support part.

Accordingly, according to one aspect, the container cover 30 may be configured to descend to a first height in a sterilization mode 1410 for the light-transmissive container and surround the container on the outer surface of the container 10, and to ascend and be located at a second height in a sterilization mode 1420 for a light-blocking container. In other words, when a non-transparent container is sterilized, the container cover 30 may ascend to prevent contact with the container.

Container Cover Deformation

The researchers of the present disclosure have discovered that when the container cover is applied in a pulsed light-based sterilization operation for the light-transmissive container, it is more preferable to improve the sterilization effect when a configuration for blocking light is in contact with the light-transmissive container. The light pulse-based sterilization mechanism may include heat generation by irradiation of high-energy pulsed light. In order for heat generated by the container cover to be properly transferred to the light-transmissive container, it may be advantageous to bring the container cover into contact with the container.

According to embodiments of the present disclosure, the container cover may be brought into contact with the container by adaptively deforming the container cover to the size and/or shape of the container.

Figure 15:
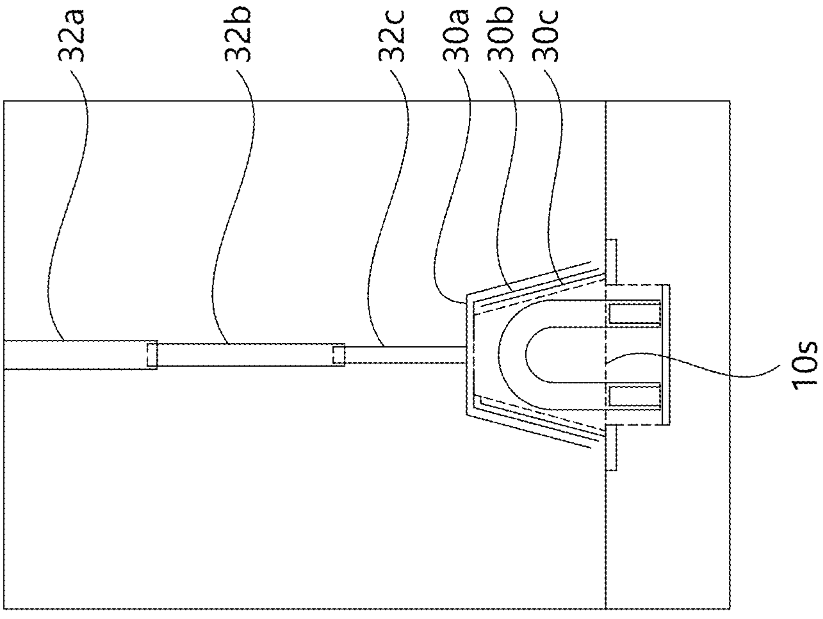
FIG. 15 is an illustration of a container cover whose size or shape is able to be adaptively deformed to the container according to one aspect.
Figure 15:
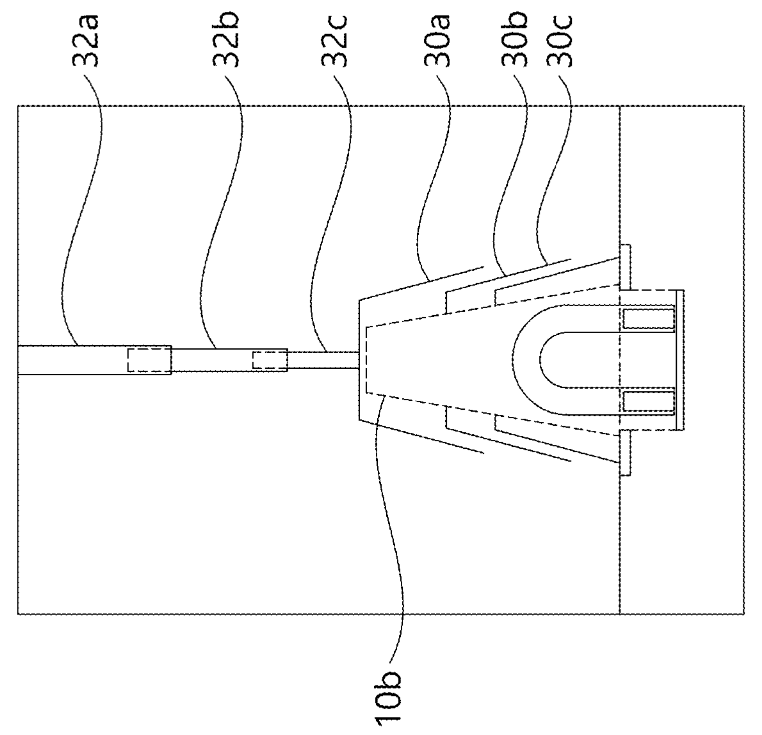

In this regard, FIG. 15 is an illustration of a container cover whose size or shape is able to be adaptively deformed to the container according to one aspect. As illustrated in FIG. 15, the container cover 30 may include: a first part 30*a* having a floor unit and a side wall connected to the floor unit; and a second part 30*b* having an additional side wall that is slidable upward and downward relative to the first part. Furthermore, a third part 30*c* having an additional side wall that may slide in an up and down direction with respect to the second part 30*b* may be further provided.

Accordingly, when sterilization is performed on the relatively large-sized container 10*b*, the second part 30*b* and/or the third part 30*c* move relative to the direction away from the first part 30*a*, thereby covering the entire container 10*b*. In this connection, the plurality of support parts 32*a*, 32*b*, and 32*c* may also adjust their relative locations so that the floor unit of the first part 30*a* of the container cover contacts a floor of the container.

On the other hand, when sterilization is performed on the relatively small-sized container 10*s*, the second part 30*b* and/or the third part 30*c* move relative to the first part 30*a* to cover the entire container 10*s*, while the relative locations of the plurality of support parts 30*a*, 32*b*, and 32*c* are adjusted so that the floor unit of the first part 30*a* of the container cover contacts the floor of the container.

In other words, by controlling the size of the container cover and the length of the support together, the floor surface of the container cover may be brought into contact with the floor surface of the container regardless of the size of the container.

Figure 16:
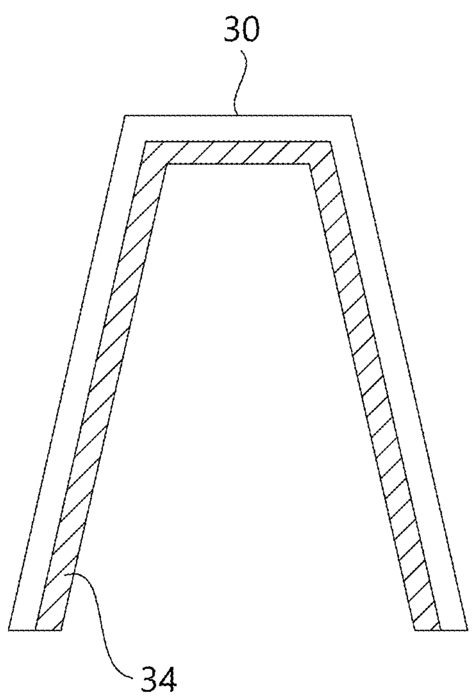
FIG. 16 is an illustration of an inner sponge unit of an exemplary container cover.

FIG. 16 is an illustration of an inner sponge unit of an exemplary container cover. As described above, in order to improve the sterilization effect, the container cover 30 may be configured so that an inner surface of the container cover contacts the outer surface of the container to be sterilized.

To this end, for example, as illustrated in FIG. 16, the container cover 30 may be provided with a sponge unit 34 on the inner surface of the container cover. Accordingly, the contact area with the outer surface of the container may be maximized by filling some of the space between the container and the container cover with the sponge unit 34.

According to one aspect, the sponge unit may be configured of a metal sponge. Light pulse-based sterilization mechanisms may include heat generation, for example by surface plasmon resonance (SPR). By disposing a metal sponge containing metal nanoparticles on the container and the container cover, the heat generated based on the SPR may be better transferred to the container, thereby improving the sterilization effect.

Figure 17:
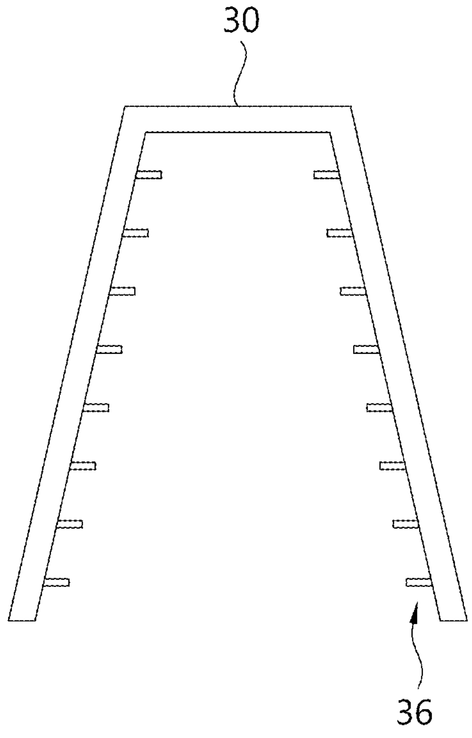
FIG. 17 is an illustration of a flexible projection of an exemplary container cover.

FIG. 17 is an illustration of a flexible projection of an exemplary container cover. As illustrated in FIG. 17, according to one aspect, the container cover 30 may be provided with a plurality of flexible projections 36 on the inner surface of the container cover. Accordingly, even when a partial space exists between the container and the container cover 30, contact between the container and the container cover may be improved by filling the space with the flexible projection.

FIGS. 1 to 6 exemplarily illustrate the structure of the sterilization device for the object to be sterilized such as a cup or tumbler having a predetermined depth from a container entrance to a bottom surface, but the technical idea of the present disclosure is not limited thereto. For example, the sterilization device for a flat container such as a plate may be included in one embodiment of the present disclosure. Although one embodiment of the present disclosure describes a container as an example, it should be understood that the sterilization device for any object to be sterilized other than a container may also be included in the technical spirit of the present disclosure. For example, in the case of the object to be sterilized that does not have an inner surface, the lamp is not inserted into the container as in the examples described above, but at least one pulsed light generating lamp is disposed on at least one side surface of an internal space to irradiate pulsed light toward the object to be sterilized. According to one aspect, a sterilization object support unit on which the object to be sterilized may be mounted may be further provided. In addition, for example, in one embodiment in which the pulsed light generating lamp is disposed on one side surface of the internal space and pulsed light is irradiated toward the object to be sterilized, when the object to be sterilized is a light-transmissive material, a sterilization object cover configured to block pulsed light irradiated from the pulsed light generating lamp and passing through the object to be sterilized made of a light-transmissive material may be provided on a side surface opposite to an opposing side surface of the pulsed light generating lamp. Accordingly, high sterilization efficiency may be expected even for the objects to the sterilized made of light-transmissive materials.

Container Material Adaptive Lamp Control

The researchers of the present disclosure have discovered that in light pulse-based sterilization, sterilization efficiency may vary depending on the material of the container to be sterilized. According to one embodiment of the present disclosure, the pulsed light generating lamp provided in the sterilization device may be operated so that an amount of energy transferred to the container to be sterilized varies depending on the material of the container.

For example, the pulsed light generating lamp may be operated so that an amount of energy transferred to the container to be sterilized is large in the order that the container is made of glass, plastic, ceramics, and metal. In other words, since high sterilization efficiency is expected for metal containers, a relatively low amount of energy may be transferred to the container. In the case of pottery, a higher amount of energy needs to be transferred than to metal, and in the case of plastic, a slightly higher amount of energy may be transferred than to pottery. In the case of glass, a higher amount of energy may be transferred than to plastic. Alternatively, as discussed above, a container cover made of a material that does not transmit light of a different material may be provided.

The pulsed light generating lamp according to one aspect may be configured to operate differently in at least one among the intensity of the light pulse, the number of times the light pulse is generated, and the generation interval of the light pulse depending on the material of the container to be sterilized. In other words, in order to transfer different amounts of energy to the object to be sterilized, the intensity of the light pulse generated from the lamp may be strengthened or weakened. Additionally, the amount of energy transfer may be controlled by varying the number of times the light pulse is generated, generating the light pulse a plurality of times, or by generating only a single light pulse. Additionally, when a plurality of light pulses are generated, controlling the time interval between light pulses may be considered. By generating light pulses at shorter intervals, it may be controlled to ensure strong sterilization.

Control of such light pulses may be appropriately performed considering at least one of the required sterilization effect, sterilization target, energy efficiency, cost for constructing equipment, or space utilization.

Visualization of Sterilization Operation

Figure 18:
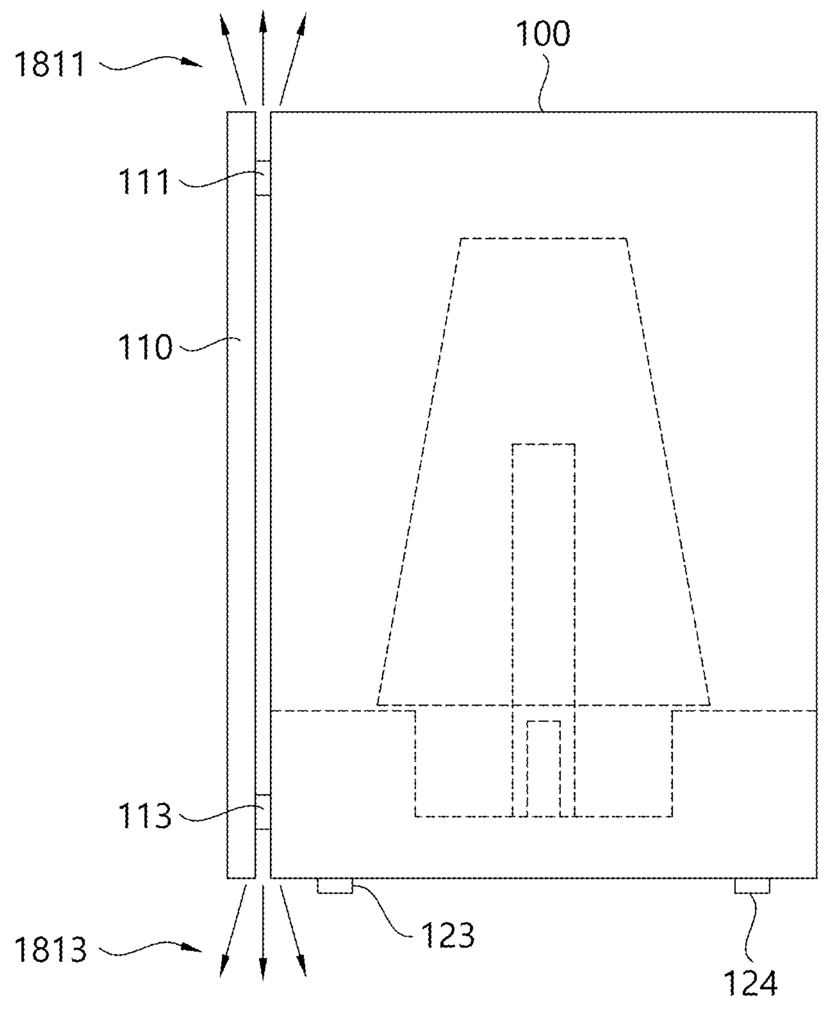
FIG. 18 is an illustration of the container sterilization device using pulsed light having a light-transmitting slit according to one embodiment of the present disclosure.

FIG. 18 is an illustration of the container sterilization device using pulsed light having a light-transmitting slit according to one embodiment of the present disclosure. Hereinafter, the sterilization device including the light-transmitting slit according to one embodiment of the present disclosure will be described in more detail with reference to FIG. 18.

As illustrated in FIGS. 1 and 18, the sterilization device according to one embodiment of the present disclosure is configured to sterilize a container using the pulsed light including a visible light band, and includes: the housing 100; the door 110; and the pulsed light generating lamp 200.

According to one aspect, the housing 100 is formed of a light blocking material and may provide the accommodation space therein. Additionally, the door 110 is formed of a light blocking material and is connected to the housing 100 in an openable and closed manner. The pulsed light generating lamp 200 is disposed inside the accommodation space of the housing and is configured to generate pulsed light.

In the case of a conventional ultraviolet-based sterilization device, ultraviolet rays are rays in a wavelength band that is distinguished from a visible light band and not recognized by the human eyes. In order to indicate that the sterilization device is operating, it is often provided with a luminescent lamp, for example blue or purple. Since the light emitted by such a luminescent lamp has a weak intensity and a small amount and has a subtle impact on the eyesight of the human body, a transparent window is often created on the front surface of the sterilization device to check a sterilization state.

On the other hand, pulsed light, such as the IPL or flash light, utilized by embodiments of the present disclosure includes a visible light band and is clearly recognized by the human eyes. Moreover, because the pulsed light generates high energy by concentration for a short period of time, the intensity of the light is not only very high, but the pulsed light also shows an instantaneous light-emitting mode. Accordingly, the pulsed light may have a significant impact on the eyesight of the human body.

Therefore, according to one aspect of the present disclosure, the housing 100 and the door 110 in which the pulsed light generating lamp 200 is built are formed of a light blocking material so that the pulsed light generated by the pulsed light generating lamp 200 is prevented from being irradiated directly toward the human body around the sterilization device, especially the eyes.

However, according to one aspect of the present disclosure, there is included a slit configured to expose pulsed light below a predetermined threshold value among the pulsed light emitted from the pulses light generating lamp 200 to the outside of the housing, allowing a user to effectively aware that sterilization is taking place. In other words, the sterilization device according to one embodiment of the present disclosure may be configured to visualize the progress of the sterilization operation to the user of the sterilization device by exposing pulsed light below a threshold value through the slit.

The pulsed light used in the sterilization device according to embodiments of the present disclosure emits bright light while blinking momentarily, as if the flash of a camera operates. Accordingly, through this operation of the lamp, the benefit of providing a user of the sterilization device or the surrounding crowd with a sense of psychological stability that the container has been clearly sterilized may be expected.

In commercial food and beverage establishments, there may be cases where the use of disposable containers is restricted for policy reasons. In such cases, when more reliable sterilization or an awareness that sterilization of containers is being carried out is delivered to customers, it may also contribute to increasing sales of the relevant food and beverage establishment.

Accordingly, the sterilization device according to one embodiment of the present disclosure may adopt at least one of various types of slits that may visualize the sterilization state by pulsed light while minimizing the impact on the eyesight of a user of the sterilization device.

The predetermined threshold value of pulsed light for exposing the slit according to embodiments of the present disclosure to the outside of the housing among the pulsed light emitted from the pulsed light generating lamp 200 may be decided taking into account of the impact on the eyesight of a user of the sterilization device and/or surrounding crowd.

As exemplarily illustrated in FIGS. 1 and 18, the slit may be formed as a gap by the protrusion units 111, 112, 113, and 114 disposed between the housing 100 and the door 110, but is not limited thereto. For example, as illustrated in FIG. 18, at least a portion of the pulsed light may be exposed toward an upper direction 1811 and/or a lower direction 1813 of the housing through the gap formed by the plurality of protrusion units 111, 112, 113, and 114.

According to another aspect, in consideration of the impact on the eyesight of the human body, a portion of the pulsed light may be exposed only toward the lower direction 1813 of the housing. As exemplarily illustrated in FIG. 18, for example, the sterilization device may include at least one support unit 123 or 124 configured to space the sterilization device from the ground, and the slit may include a downward slit exposing pulsed light toward the bottom surface of the sterilization device (1813).

Figure 19:
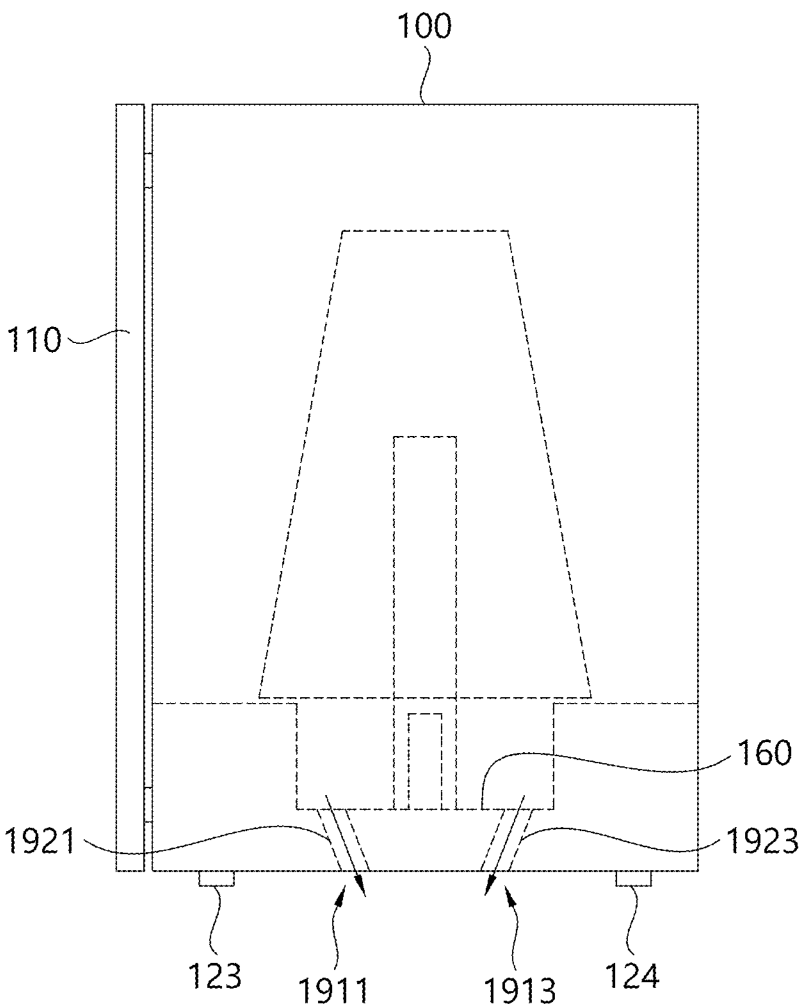
FIG. 19 is an illustration of a slit that transmits light toward the center of the bottom surface.

FIG. 19 is an illustration of a slit that transmits light toward the center of the bottom surface. According to one aspect, the downward slit provided in the sterilization device may be configured to expose pulsed light toward the center of a ground area where the sterilization device is disposed. For example, as illustrated in FIG. 19, inclined slits 1921 and 1923 penetrating to the bottom surface of the housing may be disposed in a disposition area 160 of the pulsed light generating lamp 200 inside the housing 100. Accordingly, when the pulsed light generating lamp 200 emits pulsed light, at least a portion of the emitted light may be exposed toward the center of the ground area where the sterilization device is disposed through the inclined slits 1921 and 1923. For example, pulsed light is exposed toward the center of a floor in a first direction 1911 through a first inclined slit 1921 and toward the center of the floor in a second direction 1913 through a second inclined slit 1923. Accordingly, efficient visualization of the sterilization operation is possible while minimizing the impact of pulsed light on the human eyes.

Figure 20:
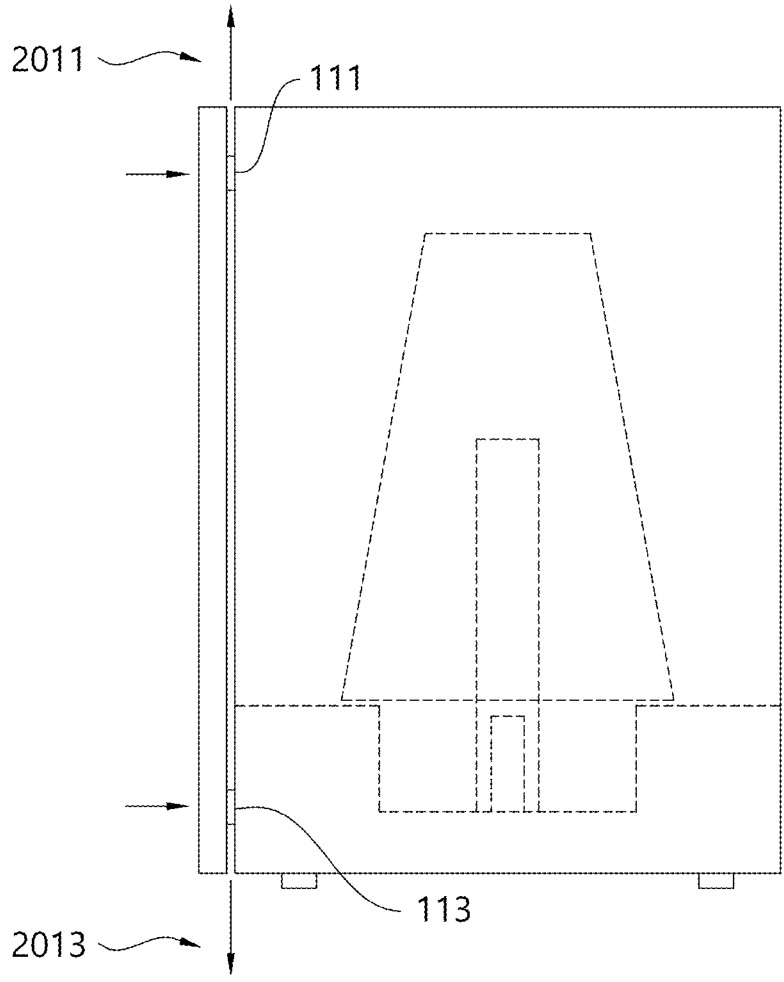
FIG. 20 is an illustration of controlling the amount of light transmitted through the slit through control of a protrusion unit.

The slit provided in the sterilization device according to one aspect of the present disclosure may be controlled to control an amount of light exposed or to stop light exposure. FIG. 20 is an illustration of controlling the amount of light transmitted through the slit through control of a protrusion unit.

According to one aspect, the slit may be configured to be closed under user control and/or to control an amount of pulsed light exposed to the outside of the housing under user control. For example, as illustrated in FIGS. 19 to 20, the slit may be formed between the housing and the door based on the protrusion units 111, 112, 113, and 114 provided on at least one of the housing 100 or the door 110. The protrusion unit may be configured so that the degree of protrusion may be changed according to user control. Accordingly, it is possible to close the slit by changing the degree to which the protrusion units protrude. As illustrated in FIG. 20, by controlling the degree to which the protrusion units 111 and 113 protrude to be smaller than in the case of FIG. 19, an amount of pulsed light exposed to an upper portion 2011 and/or a lower portion 2013 may be controlled to decrease.

Figure 21:
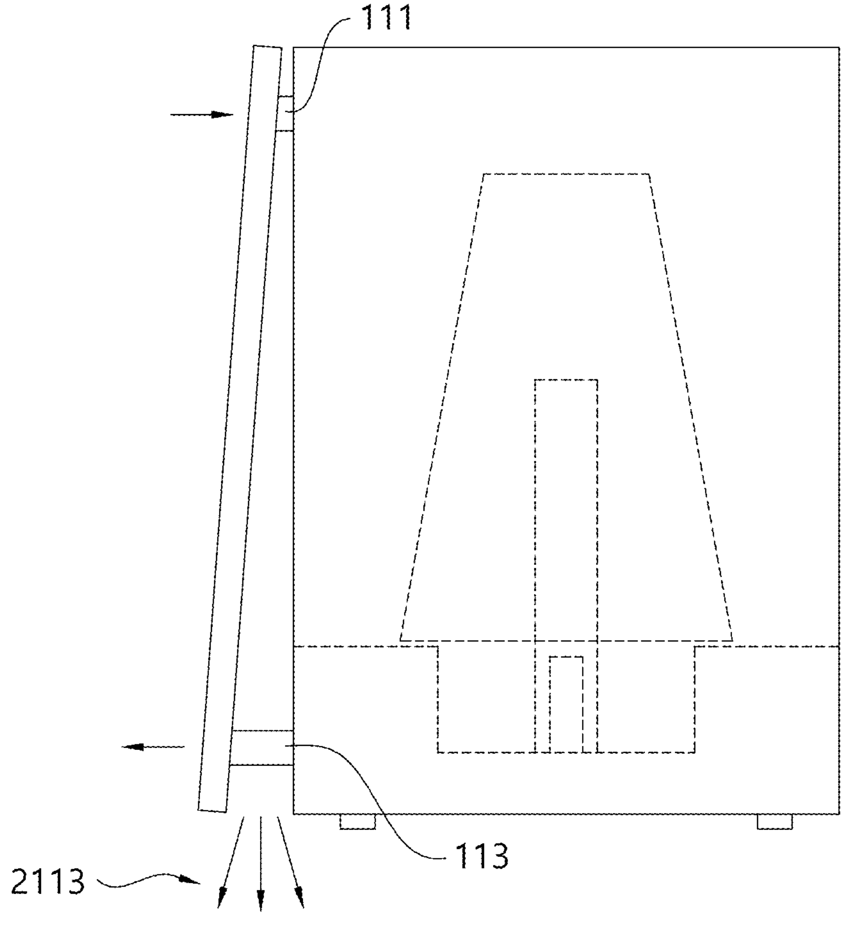
FIG. 21 is an illustration of light transmission direction control according to control of different protrusion degrees of a plurality of protrusions.

FIG. 21 is an illustration of light transmission direction control according to control of different protrusion degrees of a plurality of protrusions. As illustrated in FIG. 21, at least one of the housing 100 or the door 110 may be provided with the plurality of protrusion units 111 and 113, and the degree of protrusion of the plurality of protrusion units 111 and 113 may be changed to be different so as to control a pulsed light exposure direction of the slit formed between the housing and the door. In other words, when the degree of protrusion of the protrusion unit 111 is controlled to be relatively small, and the degree of protrusion of the protrusion unit 113 is controlled to be relatively large, the slit may be formed to face a lower direction of the sterilization device and a portion of the pulsed light may be exposed only in a downward direction (2113). Although control in the lower direction is illustrated by way of example in FIG. 21, for example, as illustrated in FIG. 1, the protrusion units 111, 112, 113, and 114 are provided at each corner of the rectangular door 110, and the degree of each protrusion is controlled differently, so that it is also possible to control the degree of pulsed light exposed in at least one of the up, down, left, right, or diagonal directions to vary. Accordingly, it may be configured to expose pulsed light in an appropriate direction adaptively to the installation environment of the sterilization device.

Structure-Integrated Sterilization Device

Figure 22:
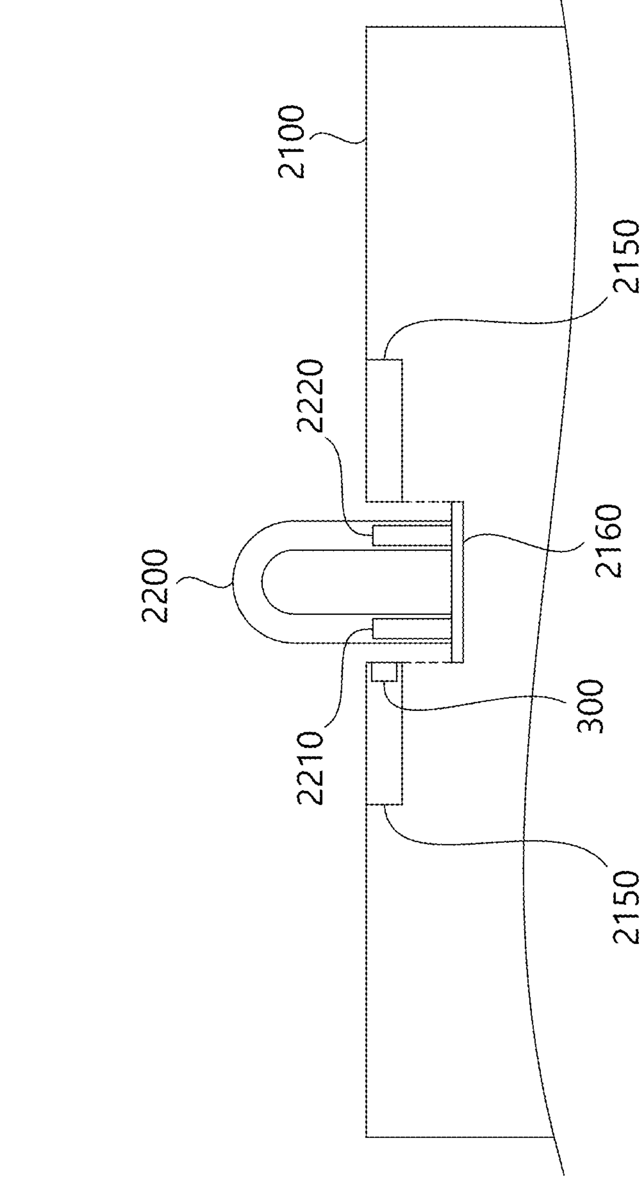
FIG. 22 is an illustration of a container sterilization device using pulsed light integrated into a stage or structure according to one embodiment of the present disclosure.

FIG. 22 is an illustration of a container sterilization device using pulsed light integrated into a stage or structure according to one embodiment of the present disclosure.

As illustrated in FIG. 22, a sterilization device 2000 according to one embodiment of the present disclosure may be configured to sterilize containers using pulsed light including a visible light band and may be integrated into a stage or structure 2100.

The sterilization device 2000 includes a container mounting area 2150 disposed on the stage or structure 2100 and a pulsed light generating lamp 2200 configured to extend from the container mounting area toward the inside of the container. The pulsed light generating lamp 2200 may be provided with a first electrode 2210 and a second electrode 2220. According to one aspect, the pulsed light generating lamp 2200 may be installed in a lamp installation area 2160 having a height lower than an upper surface of the stage or structure 2100. According to one embodiment of the present disclosure, the pulsed light generating lamp 2200 may be configured to generate pulsed light in response to the container being mounted on the container mounting area 2150. As an example, a decision of whether to mount the container may be made based on an illuminance sensor 300.

Figure 30:
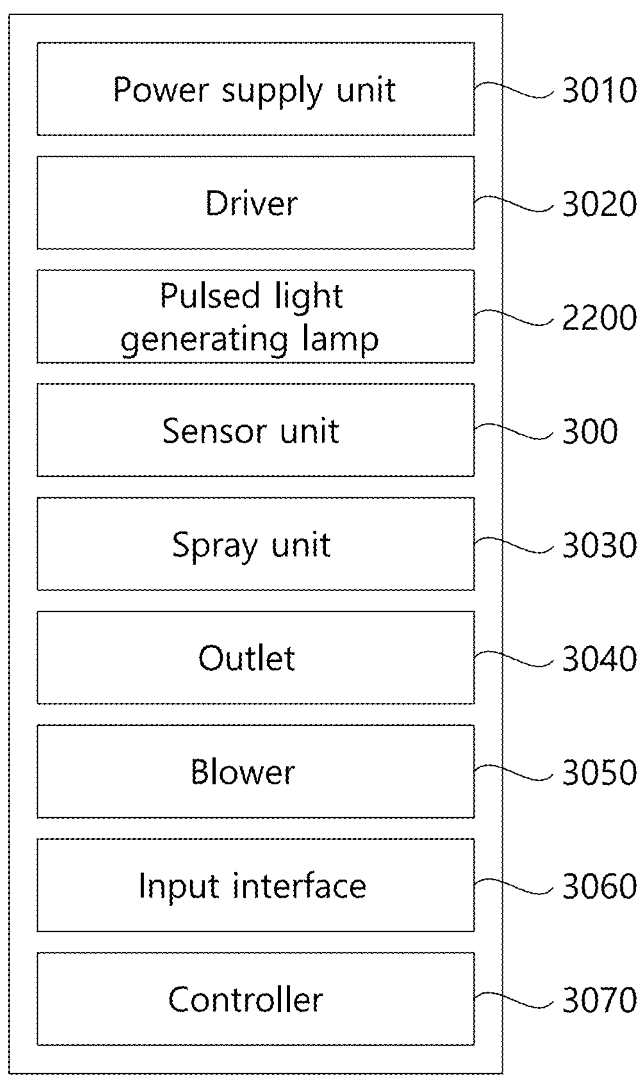
FIG. 30 is a block diagram illustrating the functional configuration of a stage or structure combined container sterilization device according to one embodiment of the present disclosure.

In this regard, FIG. 30 is a block diagram illustrating the functional configuration of a stage or structure combined container sterilization device according to one embodiment of the present disclosure. As illustrated in FIG. 30, the sterilization device 2000 according to one embodiment of the present disclosure may include at least some of a power supply unit 2010, a driver 3020, a pulsed light generating lamp 2200, a sensor unit 300, a spray unit 3030, an outlet 3040, a blower 3050, the input interface 1030, and the controller 1040.

For example, the power supply unit 3010 may refer to a power source that supplies energy necessary for the pulsed light generating lamp 2200 to generate pulsed light.

As will be described in detail later in this description, the driver 3020 may represent, for example, a configuration or structure for driving at least some configurations of the sterilization device 2000, such as a structure for causing the pulsed light generating lamp 2200 to ascend or descend.

The pulsed light generating lamp 2200 generates pulsed light to sterilize an object to be sterilized. The pulsed light generating lamp 2200 may be, for example, a xenon lamp or a xenon lamp, but is not limited thereto, and it should be understood that any type of lamp for generating pulsed light is included in the technical spirit of the present disclosure.

The sensor unit 300 includes various sensors provided in the sterilization device, such as an illuminance sensor for determining whether the container is mounted on the mounting area of the sterilization device 2000.

The spray unit 3030 includes at least one spray nozzle configured to spray a washing liquid toward the inside of the container mounted on the sterilization device 2000 according to one aspect of the present disclosure. Automatic washing of the inside of the container may be performed based on the high-pressure washing liquid sprayed from the spray unit. The spray unit may begin operation, for example, by pressurizing at least a portion of the area surrounding the spray unit by the container.

The outlet 3040 may include a path for transporting the washing liquid ejected by the spray unit and used for washing the container to a drain. According to one aspect, the pulsed light generating lamp 2200 and/or the spray unit 3030 may be provided in a receptacle having a height lower than the surface of the stage or structure 2100, and the outlet 3040 may be configured to discharge the washing liquid accumulated in the receptacle.

The blower 3050 may be configured to generate a high-pressure air flow toward the inside of the container. For example, the container may be washed by the spray unit 3030 and the washing liquid remaining in the container may be removed by a high-pressure air flow by the blower 3050.

The input interface 3060 includes a configuration for receiving input from a user to control at least one function of the sterilization device 2000 according to one embodiment of the present disclosure. For example, the input interface 3060 may include, but is not limited to, an input button or a touch screen.

The controller 3070 may include an arithmetic unit for controlling at least one configuration of the sterilization device 2000 according to one embodiment of the present disclosure. The controller 3070 may include, for example, a processor, and at least some of various arithmetic circuits may be included in the controller 3070.

For example, the configurations of the sterilization device 1000 as illustrate in FIG. 30 may be described in more detail along with a description of a plurality of embodiments in this description.

Container Mounted Sensing

Figure 23:
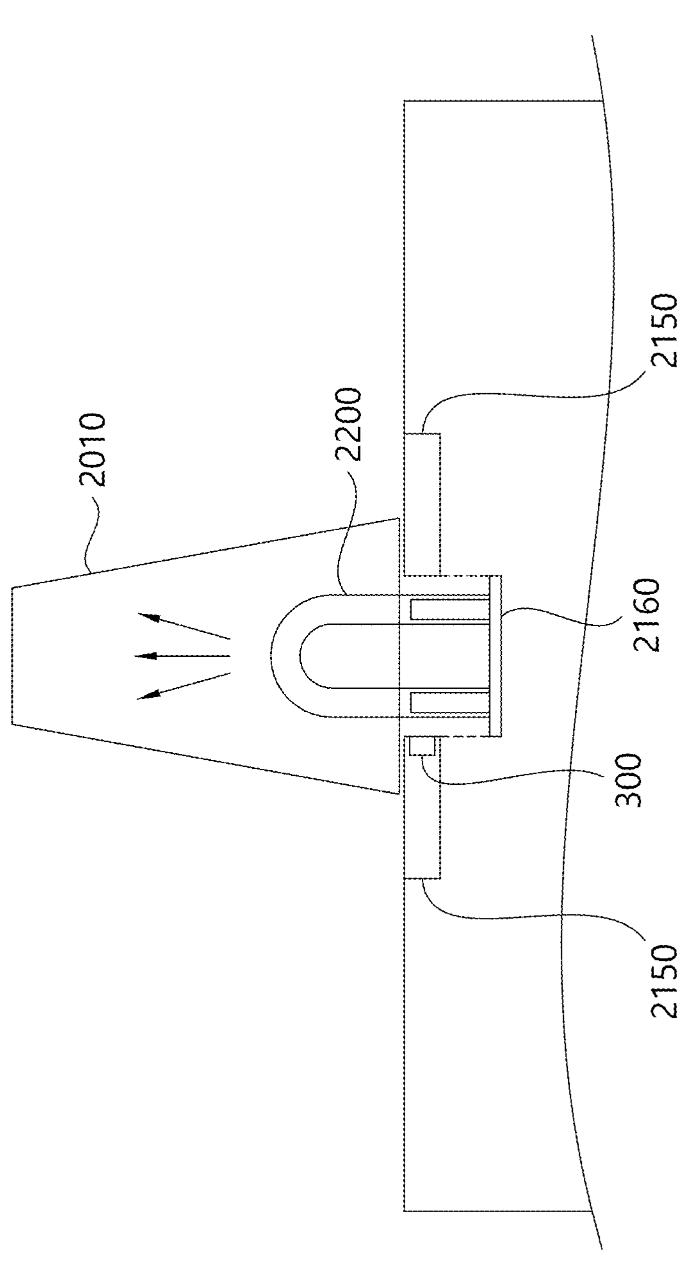
FIG. 23 exemplarily illustrates a form in which a container is mounted on the container sterilization device of FIG. 22 and pulsed light is emitted.

FIG. 23 exemplarily illustrates a form in which a container is mounted on the container sterilization device of FIG. 22 and pulsed light is emitted. As illustrated in FIG. 23, the sterilization device 2000 according to one embodiment of the present disclosure may be configured such that the pulsed light generating lamp 2200 starts emitting pulsed light in response to the container 2010 being mounted on the container mounting area 2150. According to one aspect, the sterilization device 2000 may be configured to further include the illuminance sensor 300 disposed in the container mounting area so as to be covered by the container, and the pulsed light generating lamp 2200 may be configured to generate pulsed light in response to a decision that the illuminance sensing value measured by the illuminance sensor 300 is below a predetermined threshold value. In other words, the pulsed light generating lamp 2200 is properly covered by the container 2010 to be sterilized, and the pulsed light generating lamp 2200 starts emitting light only when the illuminance value sensed by the illuminance sensor 300 is below a certain threshold value. Thereby, it is possible to prevent pulsed light from being irradiated into the eyes of a user of the sterilization device 2000 or the surrounding crowd and from affecting the eyesight. However, the way for determining container mounting is not limited to the illuminance sensor, and it should be understood that any sensors for deciding whether the container 2010 is mounted on the container mounting area 2150 are also included in the technical idea of the present disclosure.

For example, when a determination of whether to mount the container is made based on the illuminance sensor 300, in the case where the container to be sterilized is a light-transmissive material, the operation of the pulsed light generating lamp 2200 may not be activated even though the container is mounted thereon. To address this issue, for example, the sterilization device 2000 according to one aspect of the present disclosure may further include the container cover configured to surround the light-transmissive container on an outer surface of the light-transmissive container and block pulsed light from the pulsed light generating lamp in a sterilization mode for the light-transmissive container. It should be noted that at least some of the various configurations associated with the sterilization device 1000 described above in relation to the container cover may also be applied to the sterilization device 2000.

Lamp Protection

Figure 24:
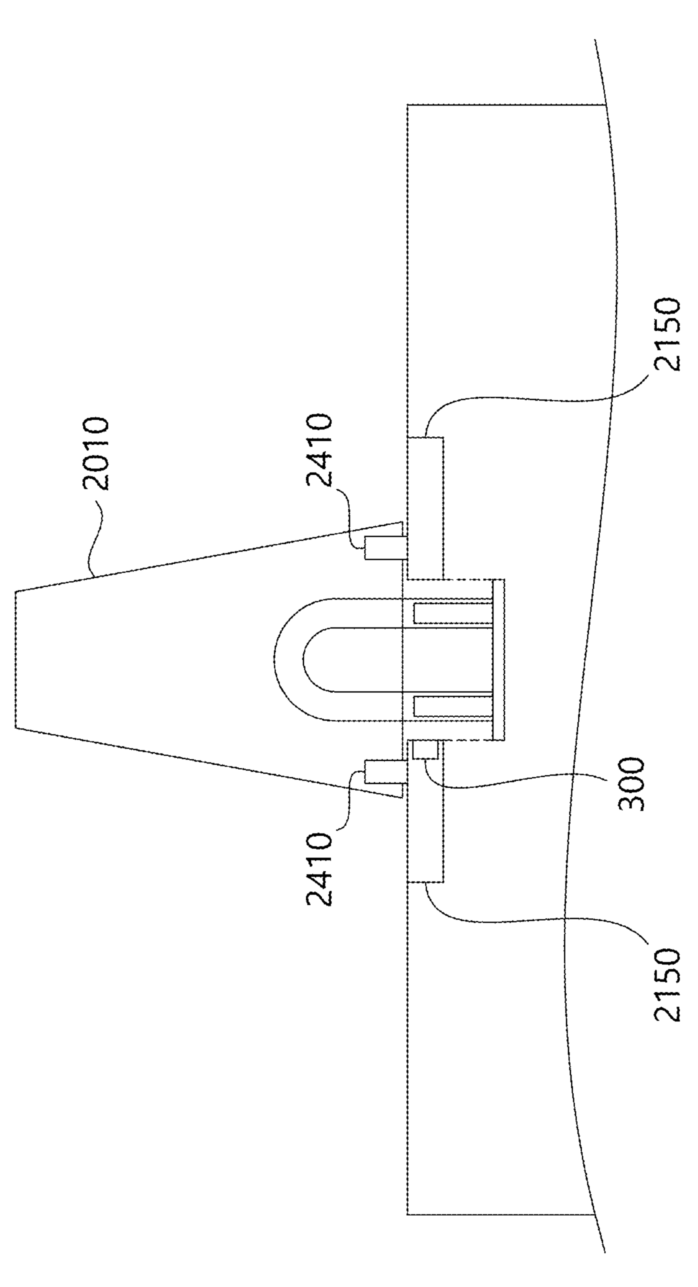
FIG. 24 exemplarily illustrates a lamp protection unit that limits movement of the container according to one aspect.
Figure 25:
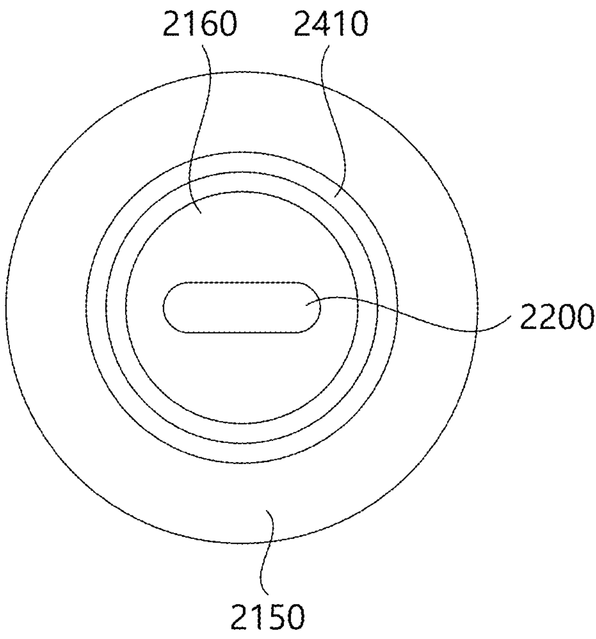
FIG. 25 is a top view of the container sterilization device provided with the lamp protection unit of FIG. 24.

FIG. 24 exemplarily illustrates a lamp protection unit that limits movement of the container according to one aspect. FIG. 25 is a top view of the container sterilization device provided with the lamp protection unit of FIG. 24. As illustrated in FIGS. 24 and 25, according to one aspect of the present disclosure, the sterilization device 2000 may further include a lamp protection unit 2410 configured to surround the pulsed light generating lamp 2200 and protrudes upward from the container mounting area 2150 to prevent the container 2010 from contacting the pulsed light generating lamp 2200. As illustrated in FIG. 25, the lamp protection unit 2410 may have, for example, a protruding hollow cylinder shape, but is not limited thereto, and may include any configuration disposed around at least a portion of the pulsed light generating lamp 2200 to prevent the container 2010 from contacting the pulsed light generating lamp 2200 while moving.

Lamp Ascending and Descending Structure

Figure 26:
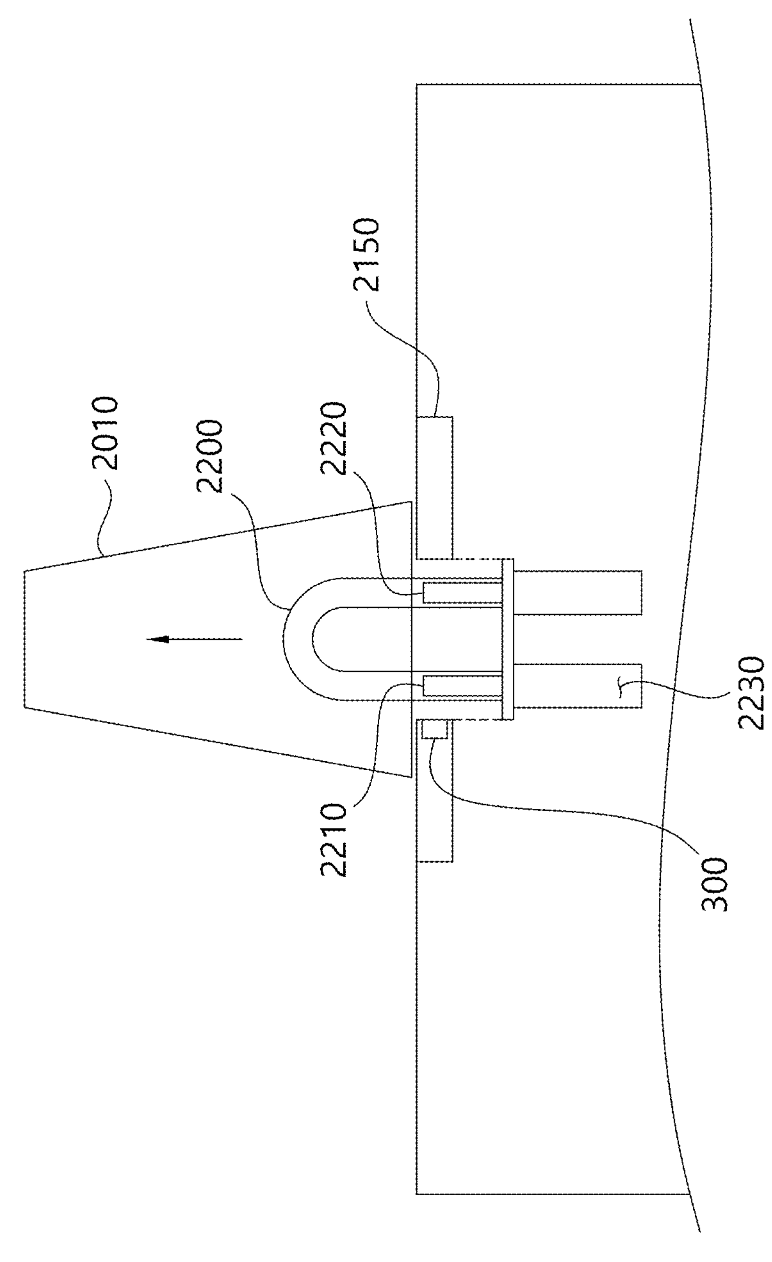
FIG. 26 exemplarily illustrates the pulsed light generating lamp that ascends in response to whether the container is mounted.
Figure 27:
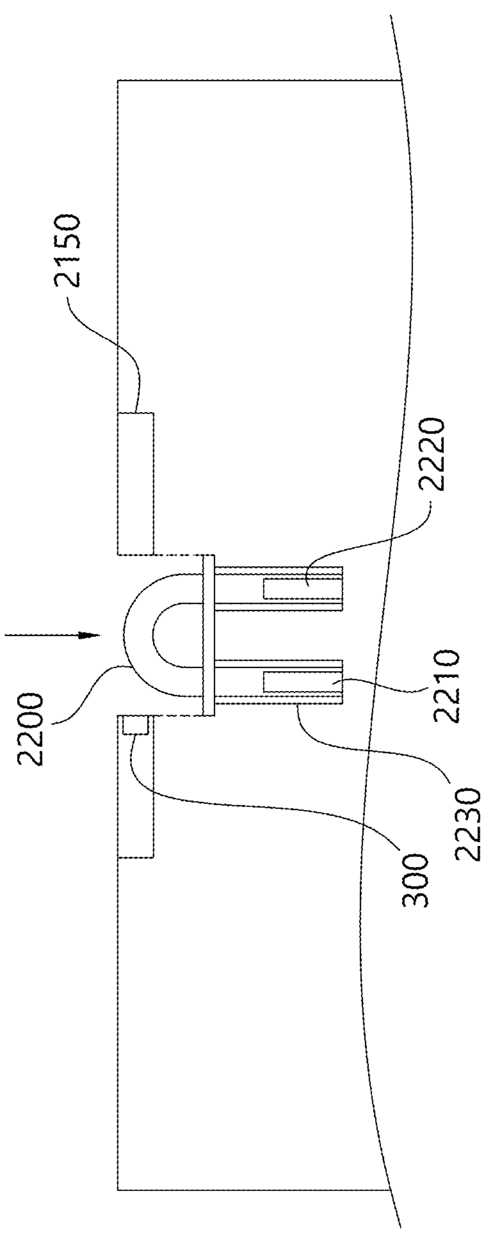
FIG. 27 exemplarily illustrates the pulsed light generating lamp descending in a state where the container is not mounted.

FIG. 26 exemplarily illustrates the pulsed light generating lamp that ascends in response to whether the container is mounted. FIG. 27 exemplarily illustrates the pulsed light generating lamp descending in a state where the container is not mounted. As illustrated in FIGS. 26 and 27, according to one aspect of the present disclosure, the pulsed light generating lamp 2200 ascends or descends depending on whether the container 2010 is mounted, so that when the container 2010 is not mounted, the pulsed light generating lamp 2200 may be inserted and located inside the stage or structure 2100. Accordingly, it is possible to prevent a safety accident or damage to the pulsed light generating lamp 2200 from occurring due to unintentional contact with the pulsed light generating lamp 2200.

As an example, the pulsed light generating lamp 2200 may be configured to be able to ascend and descend from the lamp installation area 2160, and more specifically, but non-limitingly, the pulsed light generating lamp 2200 may be configured to be placed in a lamp accommodation unit 2230 in a descended state.

As illustrated in FIG. 27, for example, in response to a decision that the illuminance sensing value measured by the illuminance sensor 300 is below a predetermined threshold value, the pulsed light generating lamp 200 may be configured to ascend from the container mounting area toward the inside of the container 2010 when the container is mounted on the container mounting area 2150.

In contrast, as illustrated in FIG. 26, for example, in response to a decision that the illuminance sensing value measured by the illuminance sensor 300 exceeds a predetermined threshold value, the pulsed light generating lamp 2200 may descend to be inserted into the lamp accommodation unit 2230 provided inside the container mounting area when the container is not mounted on the container mounting area 2150.

Receptacle

Figure 28:
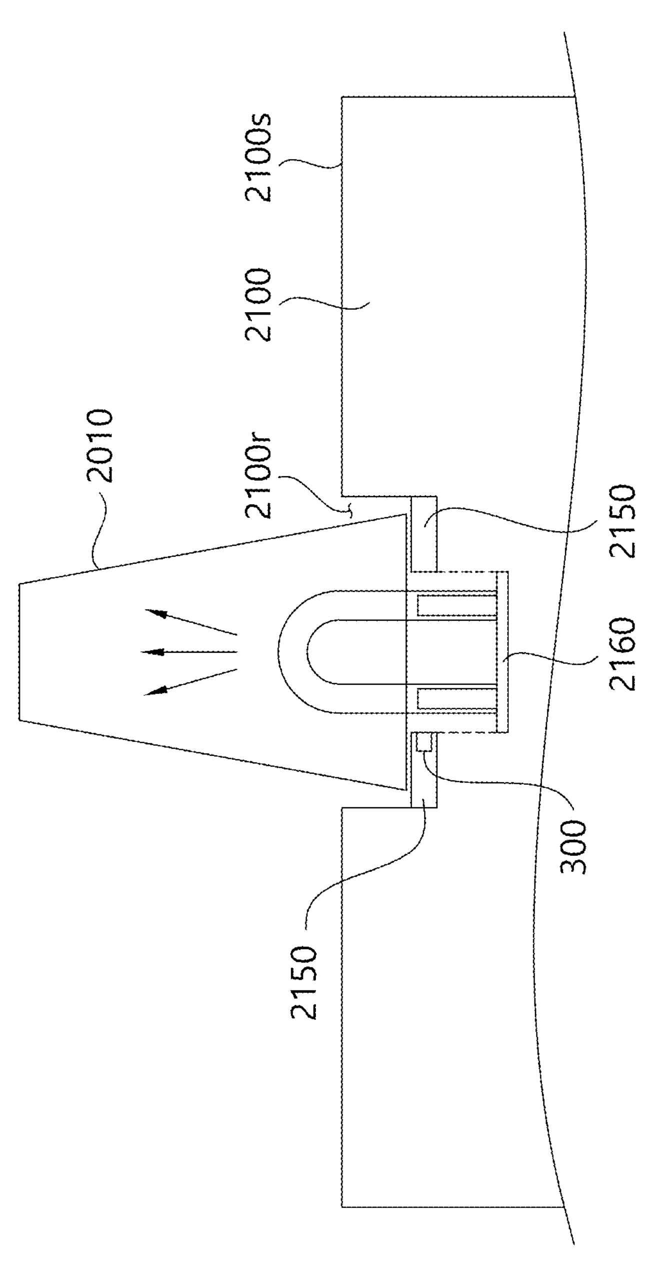
FIG. 28 is an illustration of a sterilization device provided with a receptacle on which the container is mounted.

FIG. 28 is an illustration of a sterilization device provided with a receptacle on which the container is mounted. As illustrated in FIG. 28, the sterilization device 2000 may further include a receptacle **2100*r* located in the stage or structure 2100 and formed by being recessed to have a step with respect to an upper surface 2100*s* of the stage or structure. For example, the pulsed light generating lamp 2200 may be disposed inside the receptacle 2100*r*. Herein, the container 2010 to be sterilized may be configured to be placed in the receptacle 2100*r*, thereby preventing the container 2010 from moving and coming into contact with the pulsed light generating lamp 2200**.

As illustrated in FIG. 28, even in the state where the receptacle **2100*r* is provided, the pulsed light generating lamp 2200 may be located inside the receptacle 2100*r* and disposed in a recessed area formed to have a step with respect to a container entrance contact area 2150 of the receptacle. In other words, a container installation area 2160 is disposed lower than the container entrance contact area 2150 of the receptacle, so that the shaded area of the pulsed light caused by the electrode unit of the pulsed light generating lamp 2200** is not located in the container.

Container Washing and Drying

Figure 29:
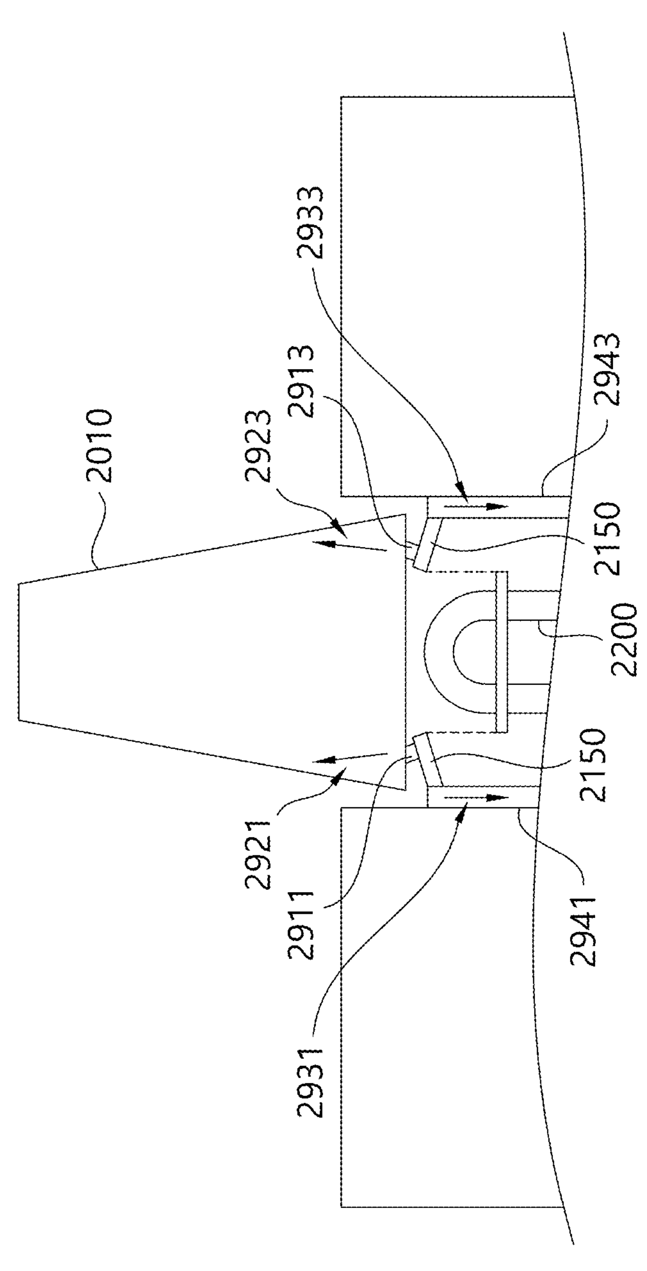
FIG. 29 is an illustration of the container sterilization device provided with a spray nozzle and outlet for washing water.

FIG. 29 is an illustration of the container sterilization device provided with a spray nozzle and outlet for washing water. As illustrated in FIG. 29, according to one aspect of the present disclosure, the sterilization device 2000 may further include spray nozzles 2911 and 2913 and outlets 2941 and 2943.

The spray nozzles 2911 and 2913 may be disposed inside the receptacle and configured to spray washing water toward the inside of the container 2010, and may include one or more first spray nozzles 2911 that spray washing water in a first direction 2921 and a second spray nozzle 2913 that sprays washing water in a second direction. According to one aspect, spraying of washing water by the spray nozzle may be activated by pressurizing any area in the vicinity of the spray nozzle, for example a container contact area 2150.

The outlets 2941 and 2943 may be configured to discharge liquid accumulating in the receptacle. For example, a first outlet 2941 may be configured to discharge washing water flowing in a first discharge direction 2931, and the second outlet 2943 may be configured to discharge washing water flowing in a second discharge direction 2933. According to one aspect, the container contact area 2150 may be inclined so that its height decreases toward a wall surface of the receptacle **2100*r*. The washing water sprayed by the spray nozzles 2911 and 2913 may be configured to complete washing of the container and descend into the receptacle 2100*r*, then flow to the outer peripheral portion of the receptacle 2100*r* along the slope of the container contact area 2150 and be discharged through the outlets 2941 and 2943. Accordingly, the degree to which washing water is contacted by the pulsed light generating lamp 2200 may be reduced. Additionally, according to one aspect, a protective cover (not shown) may be further provided to protect the pulsed light generating lamp 2200 when the spray nozzles 2911 and 2913** are operated.

As described above with reference to FIG. 30, the sterilization device 2000 according to one aspect of the present disclosure may further include the blower 3050. For example, the blower 3050 may be disposed inside the receptacle and configured to generate an air flow toward the inside of the container to remove the washing liquid caused by the spray nozzles 2911 and 2913 remaining inside the container. The disposition location of the blower 3050 is not limited to a specific location, and may be disposed in any location to remove residual washing liquid inside the container.

According to one aspect of the present disclosure, in response to the container being mounted on the container mounting area 2150, the container sterilization device 2000 may be configured such that the at least one spray nozzle 2911 or 2913 sprays washing water, the blower 3050 generates an air flow to remove the washing water inside the container, and then the pulsed light generating lamp 2200 generates pulsed light to sterilize the container. Accordingly, the sterilization device 2000 according to one aspect of the present disclosure may perform high-pressure washing and removal of remaining liquid on the container and then perform pulsed light-based sterilization by the pulsed light generating lamp 2200, thereby having the advantageous benefit of being able to perform both washing and efficient sterilization of containers within a very short period of time. Furthermore, when the sterilization device 2000 is used in a commercial food and beverage establishment, it allows customers to easily perform washing and sterilization themselves, thereby reducing the man-hours of employees and giving customers a sense of psychological stability without questioning whether washing and sterilization were performed.

Although the sterilization device 2000 according to one embodiment of the present disclosure has been described with reference to FIGS. 22 to 30, it should be understood that at least some configurations of the sterilization device 1000 previously described with reference to FIGS. 1 to 21 may also be applied to the sterilization device 2000 according to one embodiment of the present disclosure.

Hereinbefore, the embodiments of the present disclosure have been described with reference to the accompanying drawing, but the scope of protection of the present disclosure should not be construed as being limited to the drawings or embodiments. It will be understood by those skilled in the technical field that the present disclosure allows various modifications and variations without departing from the scope and spirit of the present disclosure as described in the claims below.

The above-described present disclosure has been described based on a series of functional blocks, but it is not limited by the above-described embodiment and attached drawings, and it is obvious to those skilled in the technical field to which the present disclosure pertains that embodiments may be substituted, modified, and changed in various ways within the scope of the technical ideas of the present disclosure.

The combination of the above-described embodiments is not limited to the above-described embodiments, and various forms of combinations as well as the above-described embodiments may be provided according to implementation and/or need.

In the above-described embodiments, methods are described based on a flowchart as a series of operations or blocks, but the present disclosure is not limited to the order of operations, and some operations may be performed in a different order or simultaneously. Further, those skilled in the technical field would understand that operations in the flowchart are not exclusive, another operation may be added, or one or more operations in the flowchart may be deleted without affecting the scope of the present disclosure.

The above-described embodiments include various forms of examples. It is not possible to describe all possible combinations for indicating various forms, but those skilled in the technical field would easily recognize the possibility of other combinations. Accordingly, it should be understood that the present disclosure includes all other substitutions, modifications, and changes within the scope of claims below.

What is claimed is:

1. A container sterilization device using pulsed light configured to sterilize a container using the pulsed light comprising a visible light band, the device comprising:

a housing provided with an openable door and providing an accommodation space therein;

a container mounting area disposed on at least a portion of a bottom surface of the accommodation space;

a pulsed light generating lamp configured to be extended from the container mounting area toward an inside of the container; and a container cover configured to surround the container on an outer surface of the container and block the pulsed light from the pulsed light generating lamp.

2. The device of claim 1, wherein the container sterilization device is configured so that the container cover surrounds the container only in a sterilization mode for a light-transmissive container.

3. The device of claim 2, wherein the container cover is provided separately from the housing.

4. The device of claim 2, wherein the container cover is connected to at least one side surface of the accommodation space so that a location of the container cover is able to be changed.

5. The device of claim 2, wherein the container cover is configured to: be connected to an inner ceiling of the accommodation space so that a disposition height of the container cover is adjustable; be descended to a first height in the sterilization mode for the light-transmissive container and surround the container on an outer surface of the container; and ascend and be located at a second height in the sterilization mode for a light-blocking container.

6. The device of claim 1, wherein the container cover is configured to be deformable according to at least one of the shape or size of a container to be sterilized.

7. The device of claim 6, wherein the container cover comprises:

a first part having a floor unit and a side wall connected to the floor unit; and a second part having an additional side wall that is slidable upward and downward relative to the first part.

8. The device of claim 1, wherein the container cover is configured so that an inner surface of the container cover contacts an outer surface of a container to be sterilized.

9. The device of claim 8, wherein the container cover has a sponge unit on the inner surface of the container cover.

10. The device of claim 9, wherein the sponge unit is configured of a metal sponge.

11. The device of claim 8, wherein the container cover is provided with a plurality of flexible projections on the inner surface of the container cover.

12. The device of claim 1, wherein the pulsed light generating lamp is operated so that an amount of energy transferred to a container to be sterilized is different depending on a material of the container.

13. The device of claim 12, wherein the pulsed light generating lamp is operated so that the amount of energy transferred to the container to be sterilized is large in the order that the container is made of glass, plastic, ceramics, and metal.

14. The device of claim 12, wherein the pulsed light generating lamp is configured to operate differently in at least one among the intensity of light pulse, the number of occurrences of the light pulse, and the generation interval of the light pulse depending on the material of the container to be sterilized.

* * * * *